United States Patent
Sundermann et al.

(10) Patent No.: US 7,368,470 B2
(45) Date of Patent: May 6, 2008

(54) SUBSTITUTED 3-PYRROLIDINE-INDOLE DERIVATIVES

(75) Inventors: Corinna Sundermann, Aachen (DE); Bernd Sundermann, Aachen (DE); Edward Bijsterveld, Nijmegen (NL)

(73) Assignee: Gruenenthal GmbH, Aachen (DE)

( * ) Notice: Subject to any disclaimer, the term of this patent is extended or adjusted under 35 U.S.C. 154(b) by 378 days.

(21) Appl. No.: 10/916,633

(22) Filed: Aug. 12, 2004

(65) Prior Publication Data

US 2005/0096376 A1    May 5, 2005

(30) Foreign Application Priority Data

Aug. 13, 2003   (DE) ................. 103 37 184

(51) Int. Cl.
*A61K 31/405* (2006.01)
*C07D 209/16* (2006.01)
(52) U.S. Cl. ............... 514/415; 514/340; 548/504; 548/240; 548/125; 546/276.4
(58) Field of Classification Search ............ 548/504, 548/240, 125; 546/276.4; 514/415, 340
See application file for complete search history.

(56) References Cited

U.S. PATENT DOCUMENTS

| | | | |
|---|---|---|---|
| 3,109,844 A | | 11/1963 | Perron et al. |
| 5,792,760 A | | 8/1998 | Hipskind et al. |
| 5,891,875 A | | 4/1999 | Hipskind et al. |
| 6,455,567 B1 | * | 9/2002 | Monkhouse et al. ........ 514/414 |
| 6,777,437 B2 | * | 8/2004 | Mattson et al. ............. 514/415 |
| 2005/0171143 A1 | * | 8/2005 | Tanimoto et al. ........... 514/303 |

FOREIGN PATENT DOCUMENTS

| | | |
|---|---|---|
| DE | 196 15 232 A1 | 10/1997 |
| DE | 197 56 036 A1 | 6/1999 |
| WO | WO 93/11106 | 6/1993 |
| WO | WO 94/10171 | 5/1994 |
| WO | WO 97/40038 | 10/1997 |
| WO | WO 99/10346 | 3/1999 |
| WO | WO 99/58525 | 11/1999 |
| WO | WO 00/37456 | 6/2000 |
| WO | WO 01/43740 A1 | 6/2001 |
| WO | WO 02/14317 A2 | 2/2002 |
| WO | WO 02/051837 A2 | 7/2002 |
| WO | WO 02/079151 | 10/2002 |
| WO | WO 02/079190 A1 | 10/2002 |
| WO | WO03/097598  * | 11/2003 |
| WO | WO 03/097598 A1 | 11/2003 |

OTHER PUBLICATIONS

RMF Berard, The Appropriate Use of Antidepressants in the Cancer Setting: A Review, International Medical Journal, Dec. 1996, pp. 257-259, vol. 3, No. 4, Cape town, South Africa.

Thomas M. Tzschentke, Na and 5-HT Reuptake Inhibitors and $\alpha_2$ Agonists, Analgesics, Chemistry and Pharmacology to Clinical Application, 2002, pp. 265-284, Wiley VCH.

* cited by examiner

*Primary Examiner*—Rei-tsang Shiao
(74) *Attorney, Agent, or Firm*—Crowell & Moring LLP

(57) ABSTRACT

Substituted 3-pyrrolidine-indole derivatives and methods for their production. Also pharmaceutical compositions containing these compounds and the use of these substances in methods of treatment, in particular treatment of pain and/or depression.

16 Claims, No Drawings

SUBSTITUTED 3-PYRROLIDINE-INDOLE DERIVATIVES

CROSS-REFERENCE TO RELATED APPLICATIONS

This application claims the priority of Federal Republic of Germany Patent Application No. 103 37 184.2, filed Aug. 13, 2003, the disclosure of which is expressly incorporated by reference herein.

FIELD OF THE INVENTION

The invention relates to substituted 3-pyrrolidine-indole derivatives, to methods for their production, to pharmaceutical compositions containing these compounds and to the use of these substances for producing pharmaceutical compositions, and to related treatment methods including methods for treating pain and/or depression.

BACKGROUND OF THE INVENTION

Depression is an affectivity disorder, in which a depressive syndrome predominates, depressive being associated with a low feeling or denoting a sad disposition. The anti-depressants used for therapy are also important adjuvants for pain therapy (in Analgesics—from Chemistry and Pharmacology to Clinical Application, 265-284, Wiley VCH, 2002), in particular for chronic pain, as the prolonged stress of pain may lead to a depressive mood in the patient. This is often the case with patients suffering from pain with cancer (Berard, Int. Med. J. 1996, 3/4 257-259). As there have previously been no painkillers with a clinically relevant anti-depressive active component, the anti-depressants have to be added as a medication supplementary to the analgesic dose. As patients with chronic pain frequently require a large number of different medicines, the additional dose of the anti-depressant leads to further stressing of the organism. For this reason and to increase acceptance, an analgesically effective substance with an anti-depressive active component would be particularly advantageous.

The basis of the anti-depressive efficacy is the reuptake inhibition of serotonin.

Various derivatives from the structural class of 3-pyrrolidine-indoles are already known from the literature.

WO9311106 describes 5-substituted 3-pyrrolidine-indole derivatives, wherein the radical on the pyrrolidine nitrogen represents an alkyl chain or aryl.

WO02051837 describes 3-pyrrolidine-indole derivatives as 5-$HT_6$ ligands, wherein the radical on the pyrrolidine nitrogen represents an alkyl chain, in which one carbon may also be replaced by oxygen or nitrogen, cycloalkyl, cycloheteroaryl, aryl or heteroaryl.

WO9410171 discloses 3-pyrrolidine-indole derivatives with alkyl, aryl and alkyl aryl as nitrogen substituents of the pyrrolidine as analgesically effective compounds which, however, are substituted in the 5 position.

U.S. Pat. No. 3,109,844 discloses 3-pyrrolidine-indole derivatives which carry a substituted alkyl radical on the pyrrolidine nitrogen.

WO02079190 describes 3-pyrrolidine-indole derivatives which carry a specifically substituted alkyl radical (a saturated nitrogen heterocycle) on the pyrrolidine nitrogen. These 3-pyrrolidine-indole derivatives are chemokine antagonists.

WO02079151 describes 3-pyrrolidine-indole derivatives which have an alkyl chain on the pyrrolidine nitrogen, which may be interrupted by a cyclic radical, these derivatives being chemokine antagonists.

WO0214317 discloses 3-pyrrolidine-indole derivatives, wherein a pyrazole radical is linked via an alkyl chain, which chain may also contain heteroatoms, to the pyrrolidine nitrogen.

WO0143740 discloses 3-pyrrolidine-indole derivatives, wherein an aryl radical is linked via an alkyl chain, which is interrupted by a heteroatom, to the pyrrolidine nitrogen.

WO9958525 and WO9910346 disclose 3-pyrrolidine-indole derivatives, wherein a dihydroindole radical or 3,4-dihydro-1H-benzo[1,2,6]thiadiazine-2,2-dioxide is linked via an alkyl chain to the pyrrolidine nitrogen.

U.S. Pat. No. 5,891,875 describes 3-pyrrolidine-indole derivatives, wherein a substituted morpholine radical is linked via a methylcarbonyl group to the pyrrolidine nitrogen.

U.S. Pat. No. 5,792,760 discloses 3-pyrrolidine-indole derivatives, wherein a N-benzyl-N-(3-1H-indol-3-yl-propionyl)-acetamide radical is linked via an ethylamine group to the pyrrolidine nitrogen.

WO9740038 discloses compounds, wherein the pyrrolidine nitrogen is linked to an alkyl chain or a cycloalkyl ring, a phenyl radical or a nitrogen substituent via an alkylamine chain, an alkylamide chain or an amide function.

The majority of compounds listed are described as serotonin receptor ligands or serotonin reuptake inhibitors.

SUMMARY OF THE INVENTION

One object of the invention was to make available a new structural class of anti-depressant substances which are also capable, in particular, of treating pain.

It has surprisingly now been found that substituted 3-pyrrolidine-indole derivatives of general formula I, which in addition to serotonin reuptake inhibition also exhibit noradrenalin reuptake inhibition and a sodium channel bond (BTX binding site), and have a pronounced anti-depressive and also analgesic effect.

Certain embodiments of the invention therefore relate to substituted 3-pyrrolidine-indole derivatives of general formula I

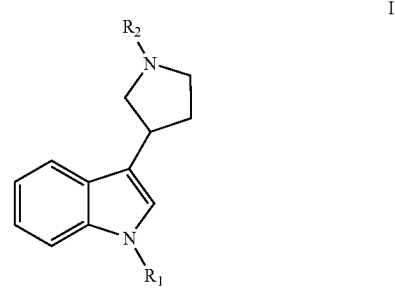

wherein
the radical $R^1$ represents H; respectively saturated or unsaturated, branched or unbranched, unsubstituted or singly or multiply substituted $C_{1-8}$-alkyl; or respectively singly or multiply substituted or unsubstituted aryl bound via $C_{1-3}$-alkyl, $C_{3-8}$-cycloalkyl or heteroaryl; $CH_2CONR^3R^4$;
the radical $R^2$ represents $COR^5$; $SO2R^6$; $CSNHR^7$; $CONHR^8$ or $CH_2CONHR^9$;

the radicals $R^3$ and $R^4$ independently of one another represent respectively saturated or unsaturated, branched or unbranched, unsubstituted or singly or multiply substituted $C_{1-8}$-alkyl;

or the radicals $R^3$ and $R^4$ together represent $CH_2CH_2OCH_2CH_2$, or $(CH_2)_{3-6}$;

the radical $R^5$ represents branched or unbranched, saturated or unsaturated, substituted or unsubstituted $C_{1-8}$-alkyl; substituted or unsubstituted aryl; substituted or unsubstituted heteroaryl; respectively saturated or unsaturated, substituted or unsubstituted cycloalkyl or heterocyclyl;

or

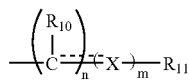

where n=1, 2, 3; m=0, 1; X=O or NH and

----- has the meaning of a single bond or a double bond;

the radical $R^6$ represents respectively substituted or unsubstituted aryl, respectively substituted or unsubstituted heteroaryl, respectively saturated or unsaturated, branched or unbranched, unsubstituted or singly or multiply substituted $C_{1-8}$-alkyl; substituted or unsubstituted, saturated or unsaturated $C_{3-8}$-cycloalkyl; or respectively singly or multiply substituted or unsubstituted aryl bound via $C_{1-3}$-alkyl, $C_{3-8}$-cycloalkyl or heteroaryl;

the radical $R^7$ represents respectively substituted or unsubstituted aryl, respectively substituted or unsubstituted heteroaryl, respectively saturated or unsaturated, branched or unbranched, unsubstituted or singly or multiply substituted $C_{1-8}$-alkyl; substituted or unsubstituted, saturated or unsaturated $C_{3-8}$ cycloalkyl; or respectively singly or multiply substituted or unsubstituted aryl bound via $C_{1-3}$-alkyl, $C_{3-8}$-cycloalkyl or heteroaryl;

the radical $R^8$ represents branched or unbranched, substituted or unsubstituted, saturated or unsaturated $C_{1-8}$-alkyl; substituted or unsubstituted, saturated or unsaturated $C_{3-8}$-cycloalkyl; respectively singly or multiply substituted or unsubstituted trifluoromethyl- or nitrosubstituted phenyl, pyrrolyl, indolyl, furyl, benzofuranyl, thienyl (thiophenyl), benzothienyl, pyrazolyl, imidazolyl, thiazolyl, oxazolyl, chromenyl, oxadiazolyl, isoxazoyl, pyridazinyl, pyrimidinyl, pyrazinyl, pyranyl, indazolyl, purinyl, indolizinyl, quinolinyl, isoquinolinyl, quinazolinyl, carbazolyl, phenazinyl, or phenothiazinyl; or respectively singly or multiply substituted or unsubstituted aryl bound via $C_{1-3}$-alkyl, $C_{3-8}$-cycloalkyl or heteroaryl;

the radical $R^9$ represents branched or unbranched, substituted or unsubstituted, saturated or unsaturated $C_{1-8}$-alkyl; substituted or unsubstituted, saturated or unsaturated $C_{3-8}$-cycloalkyl; trifluoromethyl- or nitrosubstituted phenyl; respectively singly or multiply substituted or unsubstituted pyrrolyl, indolyl, furyl, benzofuranyl, thienyl, benzothienyl, pyrazolyl, imidazolyl, thiazolyl, oxazolyl, chromenyl, oxadiazolyl, isoxazoyl, pyridazinyl, pyrimidinyl, pyrazinyl, pyranyl, indazolyl, purinyl, indolizinyl, quinolinyl, isoquinolinyl, quinazolinyl, carbazolyl, phenazinyl, or phenothiazinyl; or respectively singly or multiply substituted or unsubstituted aryl bound via $C_{1-3}$-alkyl, $C_{3-8}$-cycloalkyl or heteroaryl;

$R^{10}$ represents H; branched or unbranched, substituted or unsubstituted, saturated or unsaturated $C_{1-8}$-alkyl; respectively substituted or unsubstituted aryl or heteroaryl, respectively substituted or unsubstituted benzyl or phenethyl;

$R^{11}$ represents H; branched or unbranched, substituted or unsubstituted, saturated or unsaturated $C_{1-8}$-alkyl; respectively substituted or unsubstituted aryl or heteroaryl, or respectively singly or multiply substituted or unsubstituted aryl bound via $C_{1-3}$-alkyl, $C_{3-8}$-cycloalkyl or heteroaryl;

in the form of the racemate; the enantiomers, diastereomers, blends of the enantiomers or diastereomers or of an individual enantiomer or diastereomer; the bases and/or salts of physiologically acceptable acids or cations.

Preferred are substituted 3-pyrrolidine-indole derivatives, wherein the radical $R^1$ represents H; respectively saturated or unsaturated, branched or unbranched, unsubstituted or singly or multiply substituted $C_{1-8}$-alkyl; respectively singly or multiply substituted or unsubstituted benzyl or methylnaphthyl, particularly preferred being benzyl which is unsubstituted or singly or multiply substituted by $CF_3$, Br, F, CN, $OCH_3$ or $CH_3$; $CH_2CONR^3R^4$ and the remaining radicals have the meaning given above are preferred.

Substituted 3-pyrrolidine-indole derivatives, wherein the radical $R^2$ represents $COR^5$ and $R^5$ represents 4-propylphenyl, 3,4-dimethoxyphenyl, 2-methyl-4-trifluoromethylphenyl-3-pyridine, ethenylphenyl, 2,3-difluorophenyl, 4-tert.-butylphenyl, 2-ethoxylphenyl, 3-fluoro-4-trifluoromethylphenyl, 2,3-dimethylphenyl, phenoxyethyl, phenoxymethyl, 3,4-dichlorophenyl, 4-trifluoromethylsulphanylphenyl, 2,5-dimethoxyphenyl, 2-chloro-4-nitrophenyl, 2-chlorophenyl, 4-methyl-N-phenethyl-benzylsulphonamide, 2-chloro-5-fluoro-3-methylphenyl, 3-(2-chlorophenyl)-5-methyl-isoxazole, 5-tert.-butyl-2-methylfuran, benzo[1,2,5]oxadiazole, phenylpropyl, 2-methylsulphanyl-3-pyridine, 2-chloro-5 trifluoromethylphenyl, methoxymethyl, 4-methylphenyl, biphenyl, 4-chlorobenzyl, 2,3,4,5,6-pentafluorophenyl, 3-chlorophenyl, 4-trifluoromethylphenyl, 2,6-difluoro-3-methylphenyl, 2-methylphenyl, 4-fluorophenyl, 6-chlorochromene, 2-chloro-6-fluorophenyl, ethyl cyclopentyl, 1-(4-chlorophenyl)-5-trifluoromethylpyrazole, 2,4dichlorophenyl, 2,3-dimethylphenyl, 3-nitro-4-methylphenyl, 4-bromo-3-methylphenyl, (4-chlorophenoxy)methyl, 4-chlorophenyl, 5-methylisoxazole, 3-methoxyphenyl, 2-chlorophenylethenyl, 2-chloro-4-fluoro-3-methylphenyl, 2-fluorophenyl, 3-difluoromethylsulphanylphenyl, 2-fluoro-3-chlorophenyl, cyclopropylphenyl, 1-phenyl-5propylpyrazole, 2,6-difluorophenyl, benzo[1,3]-dioxole, 4-bromophenyl, 3-chlorothiophenyl, 2-, 3- or 4-pyridine, phenyl or 3,4-difluorophenyl and the remaining radicals have the meaning given above are also preferred.

Substituted 3-pyrrolidine-indole derivates, wherein the radical $R^2$ represents $SO_2R^6$ and $R^6$ represents 2,4,6-dimethylphenyl, 4-nitrophenyl, benzyl, 4-propylphenyl, 4-chlorophenyl, 2-trifluoromethylphenyl, 2,4-difluorophenyl or 3-trifluoromethylphenyl and the remaining radicals have the meaning given above are also preferred.

Substituted 3-pyrrolidine-indole derivatives, wherein the radical $R^2$ represents $CSNHR^7$ and the radical $R^7$ represents 3-trifluoromethylphenyl and the remaining radicals have the meaning given above are also preferred.

Substituted 3-pyrrolidine-indole derivatives, wherein the radical $R^2$ represents CONHR$^8$ and the radical $R^8$ represents 3,4-dichlorobenzyl and the remaining radicals have the meaning given above are also preferred.

Furthermore, substituted 3-pyrrolidine-indole derivates, wherein the radical $R^2$ represents CH$_2$COR$^9$ and $R^9$ represents 2,5-dimethylpyrazole, 3-cyano-4-methylthiophene, 4-trifluoromethylphenyl, 4-phenyl-5-trifluoromethylthiophene and the remaining radicals have the meaning given above are also preferred.

Particularly preferred are substituted 3-pyrrolidine-indole derivates selected from the group comprising (4-propyl-phenyl)-{3-[1-(4-trifluoromethyl-benzyl)-1H-indol-3-yl]-pyrrolidin-1-yl}-methanone
(3,4-dimethoxy-phenyl)-{3-[1-(3-methyl-butyl)-1H-indol-3-yl]-pyrrolidin-1-yl}-methanone
[3-(1-butyl-1H-indol-3-yl)-pyrrolidin-1-yl]-(2-methyl-6-trifluoromethyl-pyridin-3-yl)-methanone
1-{3-[1-(3-methoxy-benzyl)-1H-indol-3-yl]-pyrrolidin-1-yl}-3-phenyl-propenone
(2,3-difluoro-phenyl)-{3-[1-(4-trifluoromethyl-benzyl)-1H-indol-3-yl]-pyrrolidin-1-yl}-methanone
(4-tert-butyl-phenyl)-{3-[1-(3-methyl-butyl)-1H-indol-3-yl]-pyrrolidin-1-yl}-methanone
{3-[1-(4-bromo-benzyl)-1H-indol-3-yl]-pyrrolidin-1-yl}-(4-propyl-phenyl)-methanone
(2-ethoxy-phenyl)-{3-[1-(3-methoxy-benzyl)-1H-indol-3-yl]-pyrrolidin-1-yl}-methanone
[3-(1-ethyl-1H-indol-3-yl)-pyrrolidin-1-yl]-(3-fluoro-4-trifluoromethyl-phenyl)-methanone
(2,3-dimethyl-phenyl)-[3-(1-ethyl-1H-indol-3-yl)-pyrrolidin-1-yl]-methanone
1-{3-[1-(3-methoxy-benzyl)-1H-indol-3-yl]-pyrrolidin-1-yl}-2-phenoxy-propan-1-one
2-(3-chloro-phenoxy)-1-[3-(1-ethyl-1H-indol-3-yl)-pyrrolidin-1-yl]-ethanone
4-{3-[1-(2-phenoxy-propionyl)-pyrrolidin-3-yl]-indol-1-ylmethyl}-benzonitrile
N,N-dimethyl-2-{3-[1-(2,4,6-trimethyl-benzenesulphonyl)-pyrrolidin-3-yl]-indol-1-yl}-acetamide
(3,4-dichloro-phenyl)-[3-(1-ethyl-1H-indol-3-yl)-pyrrolidin-1-yl]-methanone
N,N-dimethyl-2-{3-[1-(3-trifluoromethyl-phenylthiocarbamoyl)-pyrrolidin-3-yl]-indol-1-yl}-acetamide
3-(1-dimethylcarbamoylmethyl-1H-indol-3-yl)-pyrrolidin-1-carboxylic acid 3,4-dichloro-benzylamide
[3-(1H-indol-3-yl)-pyrrolidin-1-yl]-(4-trifluoromethylsulphanyl-phenyl)-methanone
2-(3-{1-[2-(2,5-dimethoxy-phenyl)-acetyl]-pyrrolidin-3-yl}-indol-1-yl)-N,N-dimethyl-acetamide
(2-chloro-4-nitro-phenyl)-{3-[1-(3-fluoro-benzyl)-1H-indol-3-yl]-pyrrolidin-1-yl}-methanone
N,N-dimethyl-2-{3-[1-(pyridin-2-carbonyl)-pyrrolidin-3-yl]-indol-1-yl}-acetamide
cyclobutyl-[3-(1H-indol-3-yl)-pyrrolidin-1-yl]-methanone
N,N-diethyl-2-[3-(1-pentanoyl-pyrrolidin-3-yl)-indol-1-yl]-acetamide
3-[1-(4-nitrobenzenesulphonyl)-pyrrolidin-3-yl]-1H-indole
2-[3-(1-cyclopentanecarbonyl-pyrrolidin-3-yl)-indol-1-yl]-N,N-diethyl-acetamide
1-[3-(1-methyl-1H-indol-3-yl)-pyrrolidin-1-yl]-3-phenyl-propenone
(2-chloro-phenyl)-[3-(1H-indol-3-yl)-pyrrolidin-1-yl]-methanone
[3-(1-ethyl-1H-indol-3-yl)-pyrrolidin-1-yl]-pyridin-3-yl-methanone
N,N-dimethyl-2-(3-{1-[3-phenyl-2-(toluene-4-sulphonylamino)-propionyl]-pyrrolidin-3-yl}-indol-1-yl)-acetamide
N,N-dimethyl-2-[3-(1-phenylmethanesulphonyl-pyrrolidin-3-yl)-indol-1-yl]-acetamide
4-{3-[1-(2-chloro-6-fluoro-3-methyl-benzoyl)-pyrrolidin-3-yl]-indol-1-ylmethyl}-benzonitrile
[3-(2-chloro-phenyl)-5-methyl-isoxazol-4-yl]-[3-(1-ethyl-1H-indol-3-yl)-pyrrolidin-1yl]-methanone
2-{3-[1-(5-tert-butyl-2-methyl-furan-3-carbonyl)-pyrrolidin-3-yl]-indol-1-ylmethyl}-benzonitrile
4-{3-[1-(benzo[1,2,5]oxadiazole-5-carbonyl)-pyrrolidin-3-yl]-indol-1-ylmethyl}-benzonitrile
1-[3-(1-ethyl-1H-indol-3-yl)-pyrrolidin-1-yl]-3-phenyl-propan-1-one
1-{3-[1-(3-methoxy-benzyl)-1H-indol-3-yl]-pyrrolidin-1-yl}-3-phenyl-propan-1-one
[3-(1-methyl-1H-indol-3-yl)-pyrrolidin-1-yl]-(2-methylsulphanyl-pyridin-3-yl)-methanone
(2-chloro-5-trifluoromethyl-phenyl)-[3-(1-ethyl-i H-indol-3-yl)-pyrrolidin-1-yl]-methanone
(2-chloro-4-nitro-phenyl)-{3-[1-(4-trifluoromethyl-benzyl)-1H-indol-3-yl]-pyrrolidin-1 yl}-methanone
(2-chloro-pyridin-3-yl)-[3-(1-methyl-1H-indol-3-yl)-pyrrolidin-1-yl]-methanone
2-methoxy-1-{3-[1-(3-methoxy-benzyl)-1H-indol-3-yl]-pyrrolidin-1-yl}-ethanone
{3-[1-(3-fluoro-benzyl)-1H-indol-3-yl]-pyrrolidin-1-yl}-(2-methyl-6-trifluoromethylpyridin-3-yl)-methanone
{3-[1-(3-methoxy-benzyl)-1H-indol-3-yl]-pyrrolidin-1-yl}-p-tolyl-methanone
(2-methylsulphanyl-pyridin-3-yl)-[3-(1-prop-2-ynyl-1H-indol-3-yl)-pyrrolidin-1-yl]-methanone
biphenyl-4-yl-[3-(1-methyl-1H-indol-3-yl)-pyrrolidin-1-yl]-methanone
2-(4-chloro-phenyl)-1-{3-[1-(3-methoxy-benzyl)-1H-indol-3-yl]-pyrrolidin-1-yl}-ethanone
[3-(1-methyl-1H-indol-3-yl)-pyrrolidin-1-yl]-pentafluorophenyl-methanone
[3-(1-ethyl-1H-indol-3-yl)-pyrrolidin-1-yl]-(4-trifluoromethyl-phenyl)-methanone
2-[3-(1-but-2-ynyl-1H-indol-3-yl)-pyrrolidin-1-yl]-N-(2,5-dimethyl-2H-pyrazol-3-yl)-acetamide
N-(3-cyano-4-methyl-thiophen-2-yl)-2-{3-[1-(3,5-dimethyl-benzyl)-1H-indol-3-yl]pyrrolidin-1-yl}-acetamide
N,N-diethyl-2-(3-{1-[(4-trifluoromethyl-phenyl carbamoyl)-methyl]-pyrrolidin-3-yl}-indol-1-yl)-acetamide
N-(3-cyano-4-methyl-thiophen-2-yl)-2-[3-(1-ethyl-1H-indol-3-yl)-pyrrolidin-1-yl]-acetamide
2-{3-[1-(3,4-difluoro-benzyl)-1H-indol-3-yl]-pyrrolidin-1-yl}-N-(4-phenyl-5-trifluoromethyl-thiophen-3-yl)-acetamide
N,N-dimethyl-2-{3-[1-(4-propyl-benzenesulphonyl)-pyrrolidin-3-yl]-indol-1-yl}-acetamide
(2-chloro-4-nitro-phenyl)-{3-[1-(3-methoxy-benzyl)-1H-indol-3-yl]-pyrrolidin-1-yl}-methanone
3-{3-[1-(4-chloro-benzenesulphonyl)-pyrrolidin-3-yl]-indol-1-ylmethyl}-benzonitrile
1-{3-[1-(3-methoxy-benzyl)-1H-indol-3-yl]-pyrrolidin-1-yl}-3,3-dimethyl-butan-1-one
2-(4-chloro-phenyl)-1-[3-(1-methyl-1H-indol-3-yl)-pyrrolidin-1-yl]-ethanone
(2,6-difluoro-3-methyl-phenyl)-{3-[1-(3-methoxy-benzyl)-1H-indol-3-yl]-pyrrolidin-1-yl}-methanone
[3-(1-ethyl-1H-indol-3-yl)-pyrrolidin-1-yl]-o-tolyl-methanone

[3-(1-ethyl-1H-indol-3-yl)-pyrrolidin-1-yl]-(4-fluoro-phenyl)-methanone
[3-(1-butyl-1H-indol-3-yl)-pyrrolidin-1-yl]-(6-chloro-2H-chromen-3-yl)-methanone
(2-chloro-6-fluoro-phenyl)-[3-(1-naphthalen-2-ylmethyl-1H-indol-3-yl)-pyrrolidin-1-yl]-methanone
2-{3-[1-(3-cyclopentyl-propionyl)-pyrrolidin-3-yl]-indol-1-yl}-N,N-dimethyl-acetamide
[3-(2-chloro-phenyl)-5-methyl-isoxazol-4-yl]-{3-[1-(3-methoxy-benzyl)-1H-indol-3-yl]-pyrrolidin-1-yl}-methanone
[1-(4-chloro-phenyl)-5-trifluoromethyl-1H-pyrazol-4-yl]-{3-[1-(3-fluoro-benzyl)-1H-indol-3-yl]-pyrrolidin-1-yl}-methanone
[3-(1-allyl-1H-indol-3-yl)-pyrrolidin-1-yl]-p-tolyl-methanone
{3-[1-(4-fluoro-benzyl)-1H-indol-3-yl]-pyrrolidin-1-yl}-pyridin-2-yl-methanone
(3,4-dichloro-phenyl)-{3-[1-(4-trifluoromethyl-benzyl)-1H-indol-3-yl]-pyrrolidin-1-yl}-methanone
1-butyl-3-[1-(2,5-dimethoxy-benzenesulphonyl)-pyrrolidin-3-yl]-1H-indole
1-[3-(1-allyl-1H-indol-3-yl)-pyrrolidin-1-yl]-3,3-dimethyl-butan-1-one
4-{3-[1-(2-methoxy-acetyl)-pyrrolidin-3-yl]-indol-1-ylmethyl}-benzonitrile
(2,4-difluoro-phenyl)-[3-(1-ethyl-1H-indol-3-yl)-pyrrolidin-1-yl]-methanone
(2,3-dimethyl-phenyl)-{3-[1-(4-trifluoromethyl-benzyl)-1H-indol-3-yl]-pyrrolidin-1-yl}-methanone
[3-(1-butyl-1H-indol-3-yl)-pyrrolidin-1-yl]-(4-methyl-3-nitro-phenyl)-methanone
(4-bromo-3-methyl-phenyl)-{3-[1-(3-methoxy-benzyl)-1H-indol-3-yl]-pyrrolidin-1-yl}-methanone
1-[3-(1-butyl-1H-indol-3-yl)-pyrrolidin-1-yl]-2-(4-chloro-phenoxy)-ethanone
2-(4-chloro-phenyl)-1-{3-[1-(3-fluoro-benzyl)-1H-indol-3-yl]-pyrrolidin-1-yl}-ethanone
(4-chloro-phenyl)-{3-[1-(4-trifluoromethyl-benzyl)-1H-indol-3-yl]-pyrrolidin-1-yl}-methanone
[3-(1-benzyl-1H-indol-3-yl)-pyrrolidin-1-yl]-(5-methyl-isoxazol-3-yl )-methanone
1-[3-(1-benzyl-1H-indol-3-yl)-pyrrolidin-1-yl]-2-(4-chloro-phenoxy)-ethanone
[3-(1-naphthalen-2-ylmethyl-1H-indol-3-yl)-pyrrolidin-1-yl]-(4-trifluoromethylphenyl)-methanone
(3-methoxy-phenyl)-(3-[1-(4-trifluoromethyl-benzyl)-1H-indol-3-yl]-pyrrolidin-1-yl}-methanone
1-[3-(1-butyl-1H-indol-3-yl)-pyrrolidin-1-yl]-3-(2-chloro-phenyl)-propenone
1-[3-(1-methyl-1H-indol-3-yl)-pyrrolidin-1-yl]-2-phenyl-butane-1-one
(2-chloro-6-fluoro-3-methyl-phenyl)-[3-(1-methyl-1H-indol-3-yl)-pyrrolidin-1-yl]-methanone
2-{3-[1-(3-methoxy-benzoyl)-pyrrolidin-3-yl]-indol-1-yl}-N,N-dimethyl-acetamide
2-{3-[1-(2-fluoro-benzoyl)-pyrrolidin-3-yl]-indol-1-yl}-N,N-dimethyl-acetamide
(3-difluoromethylsulphanyl-phenyl)-[3-(1-naphthalen-2-ylmethyl-1H-indol-3-yl)-pyrrolidin-1-yl]-methanone
benzo[1,2,5]oxadiazol-5-yl-{3-[1-(3-fluoro-benzyl)-1H-indol-3-yl]-pyrrolidin-1-yl}-methanone
o-tolyl-{3-[1-(4-trifluoromethyl-benzyl)-1H-indol-3-yl]-pyrrolidin-1-yl}-methanone
N,N-dimethyl-2-{3-[1-(2-trifluoromethyl-benzenesulphonyl)-pyrrolidin-3-yl]-indol-1-yl}-acetamide
1-[3-(1-butyl-1H-indol-3-yl)-pyrrolidin-1-yl]-2-phenoxy-propan-1-one
(6-chloro-2-fluoro-3-methyl-phenyl)-[3-(1-naphthalen-2-ylmethyl-1H-indol-3-yl)-pyrrolidin-1-yl]-methanone
[3-(1-allyl-1H-indol-3-yl)-pyrrolidin-1-yl]-(2-methyl-6-trifluoromethyl-pyridin-3-yl)-methanone
[3-(1-butyl-1H-indol-3-yl)-pyrrolidin-1-yl]-(4-propyl-phenyl)-methanone
2-{3-[1-(4-chloro-benzoyl)-pyrrolidin-3-yl]-indol-1-yl)-N,N-dimethyl-acetamide
1-{3-[1-(3-fluoro-benzyl)-1H-indol-3-yl]-pyrrolidin-1-yl}-3-phenyl-propan-1-one
{3-[1-(2-fluoro-benzyl)-1H-indol-3-yl]-pyrrolidin-1-yl}-(1-phenyl-5-propyl-1H-pyrazol-4-yl)-methanone
3-{3-[1-(5-tert-butyl-2-methyl-furan-3-carbonyl)-pyrrolidin-3-yl]-indol-1-ylmethyl}-benzonitrile
3-[1-(2,4-difluoro-benzenesulphonyl)-pyrrolidin-3-yl]-1-(2-fluoro-benzyl)-1H-indole
2-{3-[1-(2,6-difluoro-benzoyl)-pyrrolidin-3-yl]-indol-1-yl}-N,N-dimethyl-acetamide
1-[3-(1-butyl-1H-indol-3-yl)-pyrrolidin-1-yl]-butane-1-one
4-{3-[1-(2-propyl-pentanoyl)-pyrrolidin-3-yl]-indol-1-ylmethyl}-benzonitrile
2-(4-chloro-phenoxy)-1-[3-(1-prop-2-ynyl-1H-indol-3-yl)-pyrrolidin-1-yl]-ethanone
[3-(1-methyl-1H-indol-3-yl)-pyrrolidin-1-yl]-pyridin-3-yl-methanone
3-{3-[1-(benzo[1,3]dioxole-5-carbonyl)-pyrrolidin-3-yl]-indol-1-ylmethyl}-benzonitrile
[3-(1-butyl-1H-indol-3-yl)-pyrrolidin-1-yl]-(2-chloro-5-trifluoromethyl-phenyl)-methanone
(3-chloro-phenyl)-{3-[1-(4-trifluoromethyl-benzyl)-1H-indol-3-yl]-pyrrolidin-1-yl}-methanone
2-{3-[1-(4-bromo-benzoyl)-pyrrolidin-3-yl]-indol-1-yl}-N,N-dimethyl-acetamide
3-phenyl-1-[3-(1-prop-2-ynyl-1H-indol-3-yl)-pyrrolidin-1-yl]-propenone
3-{3-[1-(3-chloro-2-fluoro-benzoyl)-pyrrolidin-3-yl]-indol-1-ylmethyl}-benzonitrile
3-{3-[1-(2-phenyl-cyclopropanecarbonyl)-pyrrolidin-3-yl]-indol-1-ylmethyl}-benzonitrile
3-{3-[1-(3-chloro-thiophene-2-carbonyl)-pyrrolidin-3-yl]-indol-1-ylmethyl}-benzonitrile
1-prop-2-ynyl-3-[1-(2-trifluoromethyl-benzenesulphonyl)-pyrrolidin-3-yl]-1H-indole
1-(2-fluoro-benzyl)-3-[1-(3-trifluoromethyl-benzenesulphonyl)-pyrrolidin-3-yl]-1H-indole
[3-(1-benzyl-1H-indol-3-yl)-pyrrolidin-1-yl]-(6-chloro-2H-chromen-3-yl)-methanone
[3-(1-benzyl-1H-indol-3-yl)-pyrrolidin-1-yl]-(3,4-difluoro-phenyl)-methanone in the form of the racemate; the enantiomers, diastereomers, blends of the enantiomers or diastereomers or of an individual enantiomer or diastereomer; the bases and/or salts of physiologically acceptable acids or cations.

According to this invention the expressions "$C_{1-8}$ alkyl" and "$C_{1-3}$ alkyl" include acyclic saturated or unsaturated hydrocarbon radicals which may be branched or straight-chained and unsubstituted or singly or multiply substituted, by 1 to 8 or 1 to 3 carbon atoms, i.e. $C_{1-8}$ alkanyls, $C_{2-8}$ alkenyls and $C_{2-8}$ alkinyls or $C_{1-3}$ alkanyls, $C_{2-3}$ alkenyls and alkinyls. Alkenyls have at least one C—C double bond and alkinyls at least one C—C triple bond. Alkyl is advantageously selected from the group comprising methyl, ethyl, n-propyl, 2-propyl, n-butyl, isobutyl, sec.-butyl, tert.-butyl, n-pentyl, isopentyl, neo-pentyl, n-hexyl, 2-hexyl, n-heptyl, n-octyl, 1,1,3,3-tetramethylbutyl; ethylenyl (vinyl), ethinyl, propenyl (—$CH_2CH$=$CH_2$, —CH=CH—$CH_3$, —C(=$CH_2$)—$CH_3$), propinyl (—CH—C≡CH), butenyl, butinyl, pentenyl, pentinyl, hexenyl, hexinyl, heptenyl, heptinyl, octenyl and octinyl.

The expression "$C_{3-8}$ cycloalkyl" represents for the purposes of this invention, cyclic hydrocarbons with 3 to 8 carbon atoms, which may be saturated or unsaturated, unsubstituted or singly or multiply substituted. $C_{3-8}$ cycloalkyl is advantageously selected from the group comprising cyclopropyl, cyclobutyl, cyclopentyl, cyclohexyl, cycloheptyl, cyclooctyl, cyclopentenyl, cyclohexenyl, cycloheptenyl und cyclooctenyl. Cycloalkyl particularly preferably represents cyclohexyl, cyclopentyl and cyclobutyl.

The expression "heterocyclyl" represents a 3-, 4-, 5-, 6- or 7-membered cyclic organic radical containing at least 1, possibly also 2, 3, 4 or 5 heteroatoms, wherein the heteroatoms may be the same or different and the cyclic radical may be saturated or unsaturated, but is not aromatic, and may be unsubstituted or singly or multiply substituted. The heterocycle may also be part of a bicyclic or polycyclic system. Preferred heteroatoms are nitrogen, oxygen and sulphur. It is preferred if the heterocyclyl radical is selected from the group comprising tetrahydrofuryl, tetrahydropyranyl, pyrrolidinyl, piperidinyl, piperazinyl and morpholinyl, wherein the bond with the compound of general structure I may be made by any ring member of the heterocyclyl radical.

According to this invention the expression "aryl" represents aromatic hydrocarbons, inter alia phenyls, naphthyls and phenanthracenyls. The aryl radicals may also be condensed with further saturated, (partially) unsaturated or aromatic ring systems. Each aryl radical may be present in an unsubstituted or singly or multiply substituted form, wherein the aryl substituents may be the same or different and in any arbitrary and possible position of the aryl. Aryl is advantageously selected from the group comprising phenyl, 1-naphthyl and 2-naphthyl which may each be unsubstituted or singly or multiply substituted.

The expression "heteroaryl" represents a 5-, 6- or 7-membered cyclic aromatic radical which contains at least 1, possibly also 2, 3, 4 or 5 heteroatoms, wherein the heteroatoms may be the same or different and the heterocycle may be unsubstituted or singly or multiply substituted; in the case of substitution on the heterocycle the heteroaryl substituents may be the same or different and in any position of the heteroaryl. The heterocycle may also be part of a bicyclic or polycyclic system. Preferred heteroatoms are nitrogen, oxygen and sulphur. It is preferred if the heteroaryl radical is selected from the group comprising pyrrolyl, indolyl, furyl (furanyl), benzofuranyl, thienyl (thiophenyl), benzothienyl, pyrazolyl, imidazolyl, chromenyl, oxadiazolyl, thiazolyl, oxazolyl, isoxazoyl, pyridinyl, pyridazinyl, pyrimidinyl, pyrazinyl, pyranyl, indolyl, indazolyl, purinyl, pyrimidinyl, indolizinyl, quinolinyl, isoquinolinyl, quinazolinyl, carbazolyl, phenazinyl, phenothiazinyl, wherein the bond with the compounds of general structure I may be made by any arbitrary and possible ring member of the heteroaryl radical. For the purposes of this invention pyridin-2-yl, pyridin-3-yl, furan-2-yl, furan-3-yl, thien-2-yl (2-thiophene), thien-3-yl (3-thiophene), isoxazol-4-yl, isoxazol-3-yl, pyrazol-3-yl, pyrazol-4-yl, chromen-3-yl and oxadiazol-3-yl, which may each be unsubstituted or singly or multiply substituted, are particularly preferred heteroaryl radicals.

For the purposes of the present invention the expression "aryl bound via $C_{1-3}$-alkyl, $C_{3-8}$-cycloalkyl or heteroaryl" means that $C_{1-3}$ alkyl and $C_{3-8}$-cycloalkyl, aryl and heteroaryl have the meanings defined above and the cycloalkyl, aryl or heteroaryl radical is bound by a $C_{1-3}$ alkyl group to the compound of general structure I.

In conjunction with "alkyl", "alkanyl", "alkenyl" and "alkinyl", the term "substituted" is taken to mean, according to this invention, the substitution of a hydrogen radical by F, Cl, Br, I, —CN, —N≡C, $NH_2$, NH-alkyl, NH-aryl, NH-heteroaryl, NH-alkyl-aryl, NH-alkyl-heteroaryl, NH-heterocyclyl, NH-alkyl-OH, N(alkyl)$_2$, N(alkyl-aryl)$_2$, N(alkyl-heteroaryl)$_2$, N(heterocyclyl)$_2$, N(alkyl-OH)$_2$, NO, $NO_2$, SH, S-alkyl, S-aryl, S-heteroaryl, S-alkyl-aryl, S-alkyl-heteroaryl, S-heterocyclyl, S-alkyl-OH, S-alkyl-SH, OH, O-alkyl, O-aryl, O-heteroaryl, O-alkyl-aryl, O-alkyl-heteroaryl, O-heterocyclyl, O-alkyl-OH, CHO, C(=O)$C_{1-6}$-alkyl, C(=S)$C_{1-6}$-alkyl, C(=O)aryl, C(=S)aryl, C(=O)$C_{1-6}$-alkyl-aryl, C(=S)$C_{1-6}$-alkyl-aryl, C(=O)-heteroaryl, C(=S)-heteroaryl, C(=O)-heterocyclyl, C(=S)-heterocyclyl, $CO_2H$, $CO_2$-alkyl, $CO_2$-alkyl-aryl, C(=O)$NH_2$, C(=O)NH-alkyl, C(=O)NH-aryl, C(=O)NH-heterocyclyl, C(=O)N(alkyl)$_2$, C(=O)N(alkyl-aryl)$_2$, C(=O)N(alkyl-heteroaryl)$_2$, C(=O)N(heterocyclyl)$_2$, SO-alkyl, $SO_2$-alkyl, $SO_2NH_2$, $SO_3H$, PO(O—$C_{1-6}$-alkyl)$_2$, Si($C_{1-6}$-alkyl)$_3$, Si($C_{3-8}$-cycloalkyl)$_3$, Si($CH_2$—$C_{3-8}$-cycloalkyl)$_3$, Si(phenyl)$_3$, cycloalkyl, aryl, heteroaryl or heterocyclyl, wherein multiply substituted radicals are taken to mean those radicals which are substituted either on different atoms or multiply, for example twice or three times, on the same atoms, for example three times on the same carbon atom as in the case of $CF_3$ or —$CH_2CF_3$ or at different positions as in the case of —CH(OH)—CH=CH—$CHCl_2$. Multiple substitution may be made with the same or with different substituents. A substituent may also, in turn, be substituted; therefore O-alkyl also comprises inter alia —O—$CH_2$—$CH_2$—O—$CH_2$—$CH_2$—OH. For the purposes of the present invention "alkyl" particularly preferably represents methyl, ethyl, propyl, —$OCH_3$ or —CN.

With respect to "aryl", "heterocyclyl", "heteroaryl" "cycloalkyl", according to this invention "singly or multiply substituted" is taken to mean the single or multiple, for example double, triple or fourfold, substitution of one or more hydrogen atoms of the ring system by F, Cl, Br, I, CN, $NH_2$, NH-alkyl, NH-aryl, NH-heteroaryl, NH-alkyl-aryl, NH-alkyl-heteroaryl, NH-heterocyclyl, NH-alkyl-OH, N(alkyl)$_2$, N(alkyl-aryl)$_2$, N(alkyl-heteroaryl)$_2$, N(heterocyclyl)$_2$, N(alkyl-OH)$_2$, NO, $NO_2$, SH, S-alkyl, S-cycloalkyl, S-aryl, S-heteroaryl, S-alkyl-aryl, S-alkyl-heteroaryl, S-heterocyclyl, S-alkyl-OH, S-alkyl-SH, OH, O-alkyl, O-cycloalkyl, O-aryl, O-heteroaryl, O-alkyl-aryl, O-alkyl-heteroaryl, O-heterocyclyl, O-alkyl-OH, CHO, C(=O)$C_{1-6}$-alkyl, C(=S)$C_{1-6}$-alkyl, C(=O)aryl, C(=S)aryl, C(=O)—$C_{1-6}$-alkyl-aryl, C(=S)$C_{1-6}$-alkyl-aryl, C(=O)-heteroaryl, C(=S)-heteroaryl, C(=O)-heterocyclyl, C(=S)-heterocyclyl, $CO_2H$, $CO_2$-alkyl, $CO_2$-alkyl-aryl, C(=O)$NH_2$, C(=O)NH-alkyl, C(=O)NH-aryl, C(=O)NH-heterocyclyl, C(=O)N(alkyl)$_2$, C(=O)N(alkyl-aryl)$_2$, C(=O)N(alkyl-heteroaryl)$_2$, C(=O)N(heterocyclyl)$_2$, S(O)-alkyl, S(O)-aryl, $SO_2$-alkyl, $SO_2$-aryl, $SO_2NH_2$, $SO_3H$, $CF_3$, =O, =S; alkyl, cycloalkyl, aryl, heteroaryl and/or heterocyclyl; on one or possibly various atoms (wherein one substituent may, in turn, possibly be substituted). The multiple substitution is made here with the same or with different substituents. Particularly preferred substituents for "aryl" are —F, —Cl, —Br, —$CF_3$, —O—$CH_3$, —O—$CH_2CH_3$, methyl, n-propyl, nitro, tert.-butyl, —CN, —$SCF_3$, phenyl and —$SCHF_2$. Particularly preferred substituents for "heteroaryl" are methyl, —$CF_3$, phenyl, 2-chlorophenyl, 4-chlorophenyl, —SCH$_3$, —Cl, —CN, n-propyl and tert.butyl. —Cl is a preferred substituent for "heterocyclyl".

According to the invention, the term salt formed with a physiologically acceptable acid refers to salts of the respective active ingredient with inorganic or organic acids which are physiologically acceptable—in particular when applied to humans and/or mammals. Hydrochloride is particularly preferred. Examples of physiologically acceptable acids are: hydrochloric acid, hydrobromic acid, sulphuric acid, methane sulphonic acid, formic acid, acetic acid, oxalic acid, succinic acid, tartaric acid, mandelic acid, fumaric acid, lactic acid, citric acid, glutamic acid, 1,1-dioxo-1,2-dihydrol$\lambda^6$-benzo[d]isothiazol-3-one (saccharic acid), monomethyl sebacic acid, 5-oxo-proline, hexane-l-sulphonic acid, nicotinic acid, 2-, 3- or 4-amino benzoic acid, 2,4,6-trimethyl-benzoic acid, a-lipoic acid, acetyl glycine, acetyl salicylic acid, hippuric acid and/or aspartic acid.

The substances according to the invention are suitable as pharmaceutical active ingredients in pharmaceutical compositions. The invention therefore also relates to pharmaceutical compositions containing at least one 3-pyrrolidine-indole derivative according to the invention and to optionally suitable additives and/or auxiliaries and/or optionally further active ingredients.

The pharmaceutical compositions according to the invention contain, in addition to at least one substituted 3-pyrrolidine-indole derivative according to the invention, optionally suitable additives and/or auxiliary agents, therefore also excipients, fillers, solvents, diluents, dyes and/or binders and may be administered as liquid pharmaceutical preparations in the form of injection solutions, drops or juices, as semisolid pharmaceutical preparations in the form of granules, tablets, pellets, patches, capsules, plasters or aerosols. The choice of auxiliary agents, etc. and the quantities thereof to be used depend on whether the pharmaceutical composition is to be applied orally, perorally, parenterally, intravenously, intraperitoneally, intradermally, intramuscularly, intranasally, buccally, rectally or topically, for example to the skin, the mucous membranes or into the eyes. Preparations in the form of tablets, dragees, capsules, granules, drops, juices and syrups are suitable for oral application, solutions, suspensions, easily reconstitutable dry preparations and sprays are suitable for parenteral, topical and inhalative applications. 3-pyrrolidine-indole derivatives according to the invention in a deposit, in dissolved form or in a plaster, optionally with the addition of agents promoting skin penetration, are suitable percutaneous application preparations. Orally or percutaneously administrable preparation forms can release the 3-pyrrolidine-indole derivatives according to the invention after a delay. In principle, other active ingredients known to the person skilled in the art may be added to the pharmaceutical compositions according to the invention.

The amount of active ingredient to be administered to the patient varies as a function of the weight of the patient, the type of application, the indication and the severity of the illness. Conventionally, 0.005 to 1,000 mg/kg, preferably 0.05 to 5 mg/kg of at least one 3-pyrrolidine-indole derivative according to the invention are applied.

In a preferred form of the pharmaceutical composition, a 3-pyrrolidine-indole derivative is contained as a pure diastereomer and/or enantiomer, as a racemate or as a non-equimolar or equimolar blend of the diastereomers and/or enantiomers.

The invention also relates to the use of a 3-pyrrolidine-indole derivative according to the invention for producing a pharmaceutical composition for treating pain, in particular acute, neuropathic or chronic pain.

The invention also relates to the use of a 3-pyrrolidine-indole derivative according to the invention for producing a pharmaceutical composition for treating depression and/or for anxiolysis.

It has surprisingly been found that the substituted 3-pyrrolidine-indole derivative of general formula I is suitable for treating cardiovascular diseases, urinary incontinence diarrhea, pruritus, alcohol and drug abuse, medicine or substance dependency, inflammations, lethargy, bulimia, anorexia, catalepsy, for use as a local anaesthetic, an anti-arrhythmic, an anti-emetic, a nootropic, and for increasing alertness and libido.

The invention therefore relates to the use of a substituted 3-pyrrolidine-indole derivative of general formula I for producing a pharmaceutical composition for treating cardiovascular diseases, urinary incontinence diarrhea, pruritus, alcohol and drug abuse, medicine dependency, inflammations, lethargy, bulimia, anorexia, catalepsy, for use as a local anaesthetic, an anti-arrhythmic, an anti-emetic, a nootropic, and for increasing alertness and libido.

The substituted 3-pyrrolidine-indole derivatives according to the invention used for producing a pharmaceutical composition for treating pain, in particular acute, neuropathic or chronic pain, depression and/or for anxiolysis, for treating cardiovascular diseases, urinary incontinence, diarrhea, pruritus, alcohol and drug abuse, substance dependency, inflammations, lethargy, bulimia, anorexia, catalepsy, for use as a local anaesthetic, an anti-arrhythmic, an anti-emetic, a nootropic, and for increasing alertness and libido are particularly preferably selected from the following group:

(4-propyl-phenyl)-{3-[1-(4-trifluoromethyl-benzyl)-1H-indol-3-yl]-pyrrolidin-1-yl}-methanone (3,4-dimethoxy-phenyl)-{3-[1-(3-methyl-butyl)-1H-indol-3-yl]-pyrrolidin-1-yl}-methanone

[3-(1-butyl-1H-indol-3-yl)-pyrrolidin-1-yl]-(2-methyl-6-trifluoromethyl-pyridin-3-yl)-methanone 1-{3-[1-(3-methoxy-benzyl)-1H-indol-3-yl]-pyrrolidin-1-yl}-3-phenyl-propenone (2,3-difluoro-phenyl)-{3-[1-(4-trifluoromethyl-benzyl)-1H-indol-3-yl]-pyrrolidin-1-yl}-methanone (4-tert-butyl-phenyl)-{3-[1-(3-methyl-butyl)-1H-indol-3-yl]-pyrrolidin-1-yl}-methanone {3-[1-(4-bromo-benzyl)-1H-indol-3-yl]-pyrrolidin-1-yl}-(4-propyl-phenyl)-methanone (2-ethoxy-phenyl)-{3-[1-(3-methoxy-benzyl)-1H-indol-3-yl]-pyrrolidin-1-yl}-methanone

[3-(1-ethyl-1H-indol-3-yl)-pyrrolidin-1-yl]-(3-fluoro-4-trifluoromethyl-phenyl)-methanone (2,3-dimethyl-phenyl)-[3-(1-ethyl-1H-indol-3-yl)-pyrrolidin-1-yl]-methanone 1-{3-[1-(3-methoxy-benzyl)-1H-indol-3-yl]-pyrrolidin-1-yl}-2-phenoxy-propan-1-one 2-(3-chloro-phenoxy)-1-[3-(1-ethyl-1H-indol-3-yl)-pyrrolidin-1-yl]-ethanone 4-{3-[1-(2-phenoxy-propionyl)-pyrrolidin-3-yl]-indol-1-ylmethyl}-benzonitrile N,N-dimethyl-2-{3-[1-(2,4,6-trimethyl-benzenesulphonyl)-pyrrolidin-3-yl]-indol-1-yl}-acetamide (3,4-dichloro-phenyl)-[3-(1-ethyl-1H-indol-3-yl)-pyrrolidin-1-yl]-methanone N,N-dimethyl-2-{3-[1-(3-trifluoromethyl-phenylthiocarbamoyl)-pyrrolidin-3-yl]-indol-1-yl}-acetamide 3-(1-dimethylcarbanmoylmethyl-1H-indol-3-yl)-pyrrolidin-1-carboxylic acid 3,4-dichloro-benzylamide

[3-(1H-indol-3-yl)-pyrrolidin-1-yl]-(4-trifluoromethylsulphanyl-phenyl)-methanone
2-(3-{1-[2-(2,5-dimethoxy-phenyl)-acetyl]-pyrrolidin-3-yl}-indol-1-yl)-N,N-dimethyl-acetamide
(2-chloro-4-nitro-phenyl)-{3-[1-(3-fluoro-benzyl)-1H-indol-3-yl]-pyrrolidin-1-yl}-methanone
N,N-dimethyl-2-{3-[1-(pyridin-2-carbonyl)-pyrrolidin-3-yl]-indol-1-yl}-acetamide
cyclobutyl-[3-(1H-indol-3-yl)-pyrrolidin-1-yl]-methanone
N,N-diethyl-2-[3-(1-pentanoyl-pyrrolidin-3-yl)-indol-1-yl]-acetamide
3-[1-(4-nitrobenzenesulphonyl)-pyrrolidin-3-yl]-1H-indole
2-[3-(1-cyclopentanecarbonyl-pyrrolidin-3-yl)-indol-1-yl]-N,N-diethyl-acetamide
1-[3-(1-methyl-1H-indol-3-yl)-pyrrolidin-1-yl]-3-phenylpropenone
(2-chloro-phenyl)-[3-(1H-indol-3-yl)-pyrrolidin-1-yl]-methanone
[3-(1-ethyl-1H-indol-3-yl)-pyrrolidin-1-yl]-pyridin-3-yl-methanone
N,N-dimethyl-2-(3-{1-[3-phenyl-2-(toluene-4-sulphonylamino)-propionyl]-pyrrolidin-3-yl}-indol-1-yl)-acetamide
N,N-dimethyl-2-[3-(1-phenylmethanesulphonyl-pyrrolidin-3-yl)-indol-1-yl]-acetamide
4-{3-[1-(2-chloro-6-fluoro-3-methyl-benzoyl)-pyrrolidin-3-yl]-indol-1-ylmethyl}-benzonitrile
[3-(2-chloro-phenyl)-5-methyl-isoxazol-4-yl]-[3-(1-ethyl-1H-indol-3-yl)-pyrrolidin-1yl]-methanone
2-{3-[1-(5-tert-butyl-2-methyl-furan-3-carbonyl)-pyrrolidin-3-yl]-indol-1-ylmethyl}-benzonitrile
4-{3-[1-(benzo[1,2,5]oxadiazole-5-carbonyl)-pyrrolidin-3-yl]-indol-1-ylmethyl}-benzonitrile
1-[3-(1-ethyl-1H-indol-3-yl)-pyrrolidin-1-yl]-3-phenyl-propan-1-one
1-{3-[1-(3-methoxy-benzyl)-1H-indol-3-yl]-pyrrolidin-1-yl}-3-phenyl-propan-1-one
[3-(1-methyl-1H-indol-3-yl)-pyrrolidin-1-yl]-(2-methylsulphanyl-pyridin-3-yl)-methanone
(2-chloro-5-trifluoromethyl-phenyl)-[3-(1-ethyl-i H-indol-3-yl)-pyrrolidin-1-yl]-methanone
(2-chloro-4-nitro-phenyl)-{3-[1-(4-trifluoromethyl-benzyl)-1H-indol-3-yl]-pyrrolidin-1 yl}-methanone
(2-chloro-pyridin-3-yl)-[3-(1-methyl-1H-indol-3-yl)-pyrrolidin-1-yl]-methanone
2-methoxy-1-{3-[1-(3-methoxy-benzyl)-1H-indol-3-yl]-pyrrolidin-1-yl}-ethanone
{3-[1-(3-fluoro-benzyl)-1H-indol-3-yl]-pyrrolidin-1-yl}-(2-methyl-6-trifluoromethylpyridin-3-yl)-methanone
{3-[1-(3-methoxy-benzyl)-1H-indol-3-yl]-pyrrolidin-1-yl}-p-tolyl-methanone
(2-methylsulphanyl-pyridin-3-yl)-[3-(1-prop-2-ynyl-1H-indol-3-yl)-pyrrolidin-1-yl]-methanone
biphenyl-4-yl-[3-(1-methyl-1H-indol-3-yl)-pyrrolidin-1-yl]-methanone
2-(4-chloro-phenyl)-1-{3-[1-(3-methoxy-benzyl)-1H-indol-3-yl]-pyrrolidin-1-yl}-ethanone
[3-(1-methyl-1H-indol-3-yl)-pyrrolidin-1-yl]-pentafluorophenyl-methanone
[3-(1-ethyl-1H-indol-3-yl)-pyrrolidin-1-yl]-(4-trifluoromethyl-phenyl)-methanone
2-[3-(1-but-2-ynyl-1H-indol-3-yl)-pyrrolidin-1-yl]-N-(2,5-dimethyl-2H-pyrazol-3-yl)-acetamide
N-(3-cyano-4-methyl-thiophen-2-yl)-2-{3-[1-(3,5-dimethyl-benzyl)-1H-indol-3-yl]pyrrolidin-1-yl}-acetamide
N,N-diethyl-2-(3-{1-[(4-trifluoromethyl-phenyl carbamoyl)-methyl]-pyrrolidin-3-yl}-indol-1-yl)-acetamide
N-(3-cyano-4-methyl-thiophen-2-yl)-2-[3-(1-ethyl-1H-indol-3-yl)-pyrrolidin-1-yl]-acetamide
2-{3-[1-(3,4-difluoro-benzyl)-1H-indol-3-yl]-pyrrolidin-1-yl}-N-(4-phenyl-5-trifluoromethyl-thiophen-3-yl)-acetamide
N,N-dimethyl-2-{3-[1-(4-propyl-benzenesulphonyl)-pyrrolidin-3-yl]-indol-1-yl}-acetamide
(2-chloro-4-nitro-phenyl)-{3-[1-(3-methoxy-benzyl)-1H-indol-3-yl]-pyrrolidin-1-yl}-methanone
3-{3-[1-(4-chloro-benzenesulphonyl)-pyrrolidin-3-yl]-indol-1-ylmethyl}-benzonitrile
1-{3-[1-(3-methoxy-benzyl)-1H-indol-3-yl]-pyrrolidin-1-yl}-3,3-dimethyl-butan-1-one
2-(4-chloro-phenyl)-1-[3-(1-methyl-1H-indol-3-yl)-pyrrolidin-1-yl]-ethanone
(2,6-difluoro-3-methyl-phenyl)-{3-[1-(3-methoxy-benzyl)-1H-indol-3-yl]-pyrrolidin-1-yl}-methanone
[3-(1-ethyl-1H-indol-3-yl)-pyrrolidin-1-yl]-o-tolyl-methanone
[3-(1-ethyl-1H-indol-3-yl)-pyrrolidin-1-yl]-(4-fluoro-phenyl)-methanone
[3-(1-butyl-1H-indol-3-yl)-pyrrolidin-1-yl]-(6-chloro-2H-chromen-3-yl)-methanone
(2-chloro-6-fluoro-phenyl)-[3-(1-naphthalen-2-ylmethyl-1H-indol-3-yl)-pyrrolidin-1-yl]-methanone
2-{3-[1-(3-cyclopentyl-propionyl)-pyrrolidin-3-yl]-indol-1-yl}-N,N-dimethyl-acetamide
[3-(2-chloro-phenyl)-5-methyl-isoxazol-4-yl]-{3-[1-(3-methoxy-benzyl)-1H-indol-3-yl]-pyrrolidin-1-yl}-methanone
[1-(4-chloro-phenyl)-5-trifluoromethyl-1H-pyrazol-4-yl]-{3-[1-(3-fluoro-benzyl)-1H-indol-3-yl]-pyrrolidin-1-yl}-methanone
[3-(1-allyl-1H-indol-3-yl)-pyrrolidin-1-yl]-p-tolyl-methanone
{3-[1-(4-fluoro-benzyl)-1H-indol-3-yl]-pyrrolidin-1-yl}-pyridin-2-yl-methanone
(3,4-dichloro-phenyl)-{3-[1-(4-trifluoromethyl-benzyl)-1H-indol-3-yl]-pyrrolidin-1-yl}-methanone
1-butyl-3-[1-(2,5-dimethoxy-benzenesulphonyl)-pyrrolidin-3-yl]-1H-indole
1-[3-(1-allyl-1H-indol-3-yl)-pyrrolidin-1-yl]-3,3-dimethyl-butan-1-one
4-{3-[1-(2-methoxy-acetyl)-pyrrolidin-3-yl]-indol-1-ylmethyl}-benzonitrile
(2,4-difluoro-phenyl)-[3-(1-ethyl-1H-indol-3-yl)-pyrrolidin-1-yl]-methanone
(2,3-dimethyl-phenyl)-{3-[1-(4-trifluoromethyl-benzyl)-1H-indol-3-yl]-pyrrolidin-1-yl}-methanone
[3-(1-butyl-1H-indol-3-yl)-pyrrolidin-1-yl]-(4-methyl-3-nitro-phenyl)-methanone
(4-bromo-3-methyl-phenyl)-{3-[1-(3-methoxy-benzyl)-1H-indol-3-yl]-pyrrolidin-1-yl}-methanone
1-[3-(1-butyl-1H-indol-3-yl)-pyrrolidin-1-yl]-2-(4-chlorophenoxy)-ethanone
2-(4-chloro-phenyl)-1-{3-[1-(3-fluoro-benzyl)-1H-indol-3-yl]-pyrrolidin-1-yl}-ethanone
(4-chloro-phenyl)-{3-[1-(4-trifluoromethyl-benzyl)-1H-indol-3-yl]-pyrrolidin-1-yl}-methanone
[3-(1-benzyl-1H-indol-3-yl)-pyrrolidin-1-yl]-(5-methyl-isoxazol-3-yl )-methanone
1-[3-(1-benzyl-1H-indol-3-yl)-pyrrolidin-1-yl]-2-(4-chlorophenoxy)-ethanone

[3-(1-naphthalen-2-ylmethyl-1H-indol-3-yl)-pyrrolidin-1-yl]-(4-trifluoromethylphenyl)-methanone
(3-methoxy-phenyl)-(3-[1-(4-trifluoromethyl-benzyl)-1H-indol-3-yl]-pyrrolidin-1-yl}-methanone
1-[3-(1-butyl-1H-indol-3-yl)-pyrrolidin-1-yl]-3-(2-chloro-phenyl)-propenone
1-[3-(1-methyl-1H-indol-3-yl)-pyrrolidin-1-yl]-2-phenyl-butane-1-one
(2-chloro-6-fluoro-3-methyl-phenyl)-[3-(1-methyl-1H-indol-3-yl)-pyrrolidin-1-yl]-methanone
2-{3-[1-(3-methoxy-benzoyl)-pyrrolidin-3-yl]-indol-1-yl}-N,N-dimethyl-acetamide
2-{3-[1-(2-fluoro-benzoyl)-pyrrolidin-3-yl]-indol-1-yl}-N,N-dimethyl-acetamide
(3-difluoromethylsulphanyl-phenyl)-[3-(1-naphthalen-2-yl-methyl-1H-indol-3-yl)-pyrrolidin-1-yl]-methanone
benzo[1,2,5]oxadiazol-5-yl-{3-[1-(3-fluoro-benzyl)-1H-indol-3-yl]-pyrrolidin-1-yl}-methanone
o-tolyl-{3-[1-(4-trifluoromethyl-benzyl)-1H-indol-3-yl]-pyrrolidin-1-yl}-methanone
N,N-dimethyl-2-{3-[1-(2-trifluoromethyl-benzenesulphonyl)-pyrrolidin-3-yl]-indol-1-yl}-acetamide
1-[3-(1-butyl-1H-indol-3-yl)-pyrrolidin-1-yl]-2-phenoxy-propan-1-one
(6-chloro-2-fluoro-3-methyl-phenyl)-[3-(1-naphthalen-2-yl-methyl-1H-indol-3-yl)-pyrrolidin-1-yl]-methanone
[3-(1-allyl-1H-indol-3-yl)-pyrrolidin-1-yl]-(2-methyl-6-trif-luoromethyl-pyridin-3-yl)-methanone
[3-(1-butyl-1H-indol-3-yl)-pyrrolidin-1-yl]-(4-propyl-phenyl)-methanone
2-{3-[1-(4-chloro-benzoyl)-pyrrolidin-3-yl]-indol-1-yl)-N,N-dimethyl-acetamide
1-{3-[1-(3-fluoro-benzyl)-1H-indol-3-yl]-pyrrolidin-1-yl}-3-phenyl-propan-1-one
{3-[1-(2-fluoro-benzyl)-1H-indol-3-yl]-pyrrolidin-1-yl}-(1-phenyl-5-propyl-1H-pyrazol-4-yl)-methanone
3-{3-[1-(5-tert-butyl-2-methyl-furan-3-carbonyl)-pyrrolidin-3-yl]-indol-1-ylmethyl}-benzonitrile
3-[1-(2,4-difluoro-benzenesulphonyl)-pyrrolidin-3-yl]-1-(2-fluoro-benzyl)-1H-indole
2-{3-[1-(2,6-difluoro-benzoyl)-pyrrolidin-3-yl]-indol-1-yl}-N,N-dimethyl-acetamide
1-[3-(1-butyl-1H-indol-3-yl)-pyrrolidin-1-yl]-butane-1-one
4-{3-[1-(2-propyl-pentanoyl)-pyrrolidin-3-yl]-indol-1-ylmethyl}-benzonitrile
2-(4-chloro-phenoxy)-1-[3-(1-prop-2-ynyl-1H-indol-3-yl)-pyrrolidin-1-yl]-ethanone
[3-(1-methyl-1H-indol-3-yl)-pyrrolidin-1-yl]-pyridin-3-yl-methanone
3-{3-[1-(benzo[1,3]dioxole-5-carbonyl)-pyrrolidin-3-yl]-indol-1-ylmethyl}-benzonitrile
[3-(1-butyl-1H-indol-3-yl)-pyrrolidin-1-yl]-(2-chloro-5-trif-luoromethyl-phenyl)-methanone
(3-chloro-phenyl)-{3-[1-(4-trifluoromethyl-benzyl)-1H-indol-3-yl]-pyrrolidin-1-yl}-methanone
2-{3-[1-(4-bromo-benzoyl)-pyrrolidin-3-yl]-indol-1-yl}-N,N-dimethyl-acetamide
3-phenyl-1-[3-(1-prop-2-ynyl-1H-indol-3-yl)-pyrrolidin-1-yl]-propenone
3-{3-[1-(3-chloro-2-fluoro-benzoyl)-pyrrolidin-3-yl]-indol-1-ylmethyl}-benzonitrile
3-{3-[1-(2-phenyl-cyclopropanecarbonyl)-pyrrolidin-3-yl]-indol-1-ylmethyl}-benzonitrile
3-{3-[1-(3-chloro-thiophene-2-carbonyl)-pyrrolidin-3-yl]-indol-1-ylmethyl}-benzonitrile
1-prop-2-ynyl-3-[1-(2-trifluoromethyl-benzenesulphonyl)-pyrrolidin-3-yl]-1H-indole
1-(2-fluoro-benzyl)-3-[1-(3-trifluoromethyl-benzenesulpho-nyl)-pyrrolidin-3-yl]-1H-indole
[3-(1-benzyl-1H-indol-3-yl)-pyrrolidin-1-yl]-(6-chloro-2H-chromen-3-yl)-methanone
[3-(1-benzyl-1H-indol-3-yl)-pyrrolidin-1-yl]-(3,4-difluoro-phenyl)-methanone in the form of the racemate, the pure stereoisomers, the enantiomers and diastereomers, in any mixing ratio; in the form of its acids or its bases or in the form of its salts, in particular the physiologically acceptable salts or salts of physiologically acceptable acids or cations; or in the form of its solvates, in particular the hydrates, and optionally containing suitable additives and/or auxiliaries and/or optionally further active ingredients.

The invention also relates to a method for producing a 3-pyrrolidine-indole derivative according to the invention.

3-pyrrolidine-indole derivatives of general formula I are produced according to the following diagram:

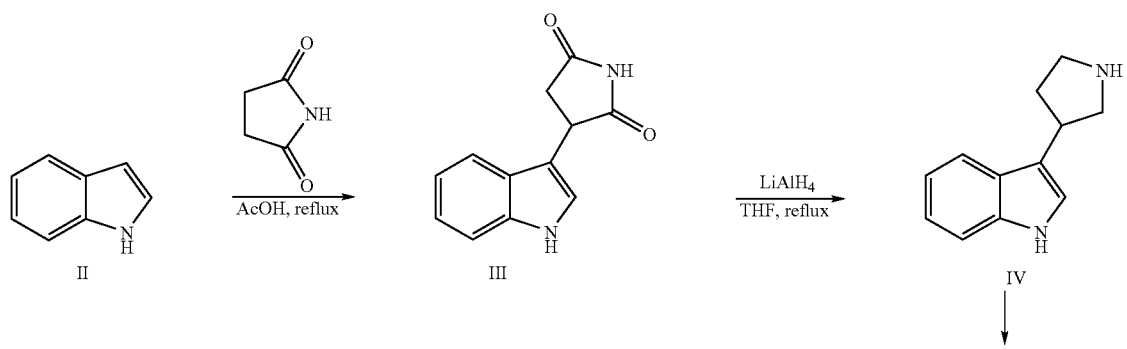

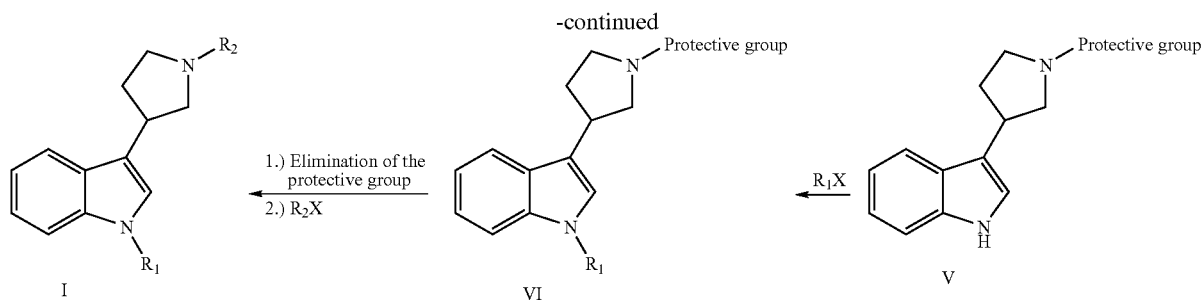

Here, indole (II) was reacted with maleinimide in a manner known per se by adding acetic acid and then reacted with LiAlH$_4$ to form 3-pyrrolidin-3-yl-indole (III). After protecting the pyrrolidine nitrogen with a protecting group known per se, preferably the Boc protecting group, the indole nitrogen was alkylated by adding an alkylation agent, preferably an alkyl halide or a benzyl halide, for example 3-fluorobenzyl bromide. After eliminating the protecting group, the pyrrolidine nitrogen was reacted with a 2-chloroacetamide or a 2-bromoacetamide, for example 2-chloro-N-(4-trifluoromethylphenyl)-acetamide, an acid chloride, for example 2-chlorobenzoyl chloride, an isocyanate, for example 1,2-dichloro-4-isocyanatomethyl-benzene, or an isothiocyanate, for example 1-isothiocyanato-3-trifluoromethyl-benzene. In the event that R$^1$ represented H, IV was reacted directly by reaction with a 2-chloroacetamide or a 2-bromoacetamide, for example 2-chloro-N-(4-trifluoromethylphenyl)-acetamide, an acid chloride, for example 2-chlorobenzoylchloride, an isocyanate, for example 1,2-dichloro-4-isocyanatomethyl-benzene, or an isothiocyanate, for example 1-isothiocyanato-3-trifluoromethyl-benzene, to form compounds of general formula I.

EXAMPLES

Example 1

Synthesis of (2-chloro-4-nitro-phenyl)-{3-[1-(3-fluoro-benzyl)-1H-indol-3-yl]-pyrrolidin-1-yl}methanone (Compound 20)

1st Stage:

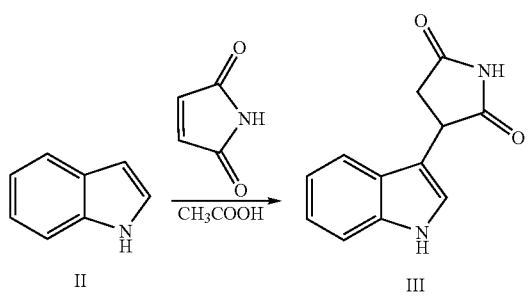

220 ml acetic acid were added to a mixture of 29.5 g (251 mmol) indole (II) and 24.4 g (251 mmol) maleinimide. The reaction mixture was heated under reflux for 3 days under a nitrogen atmosphere. After removing the solvent, 500 ml ethyl acetate were added and the mixture was extracted twice with 250 ml aqueous NaHCO$_3$ solution. The aqueous phase was extracted with 500 ml ethyl acetate. The purified organic phases were dried over Na$_2$SO$_4$. The crude product was purified via column chromatography (silica gel, ethyl acetate/hexane 1:1 followed by dichloromethane (DCM) followed by Et$_3$N/DCM/MeOH 1:89:10). 25.7 g (48%) of III were obtained.

2nd Stage:

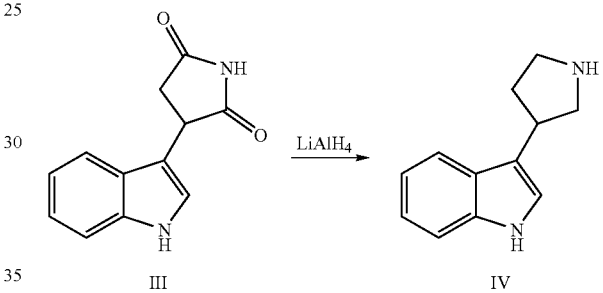

100 ml dry tetrahydrofuran (THF) were dissolved in 15.7 g (414 mmol) LiAlH$_4$. A solution of 17.7 g (82.6 mmol) of III in 250 ml dry THF was added dropwise within 30 min. The reaction mixture was heated overnight under reflux under a nitrogen atmosphere. 30 ml ethyl acetate were carefully added with ice cooling. After 1 hour 15 ml water were carefully added and, after further stirring at ambient temperature, 15 ml of an aqueous 2 N NaOH solution were added. The reaction mixture was heated under reflux and a further 50 ml water were added. After a further 2 hours the reaction mixture was cooled to ambient temperature and filtered. The residue was washed with THF. 16.3 g of IV were obtained and this was used without further purification.

3rd Stage:

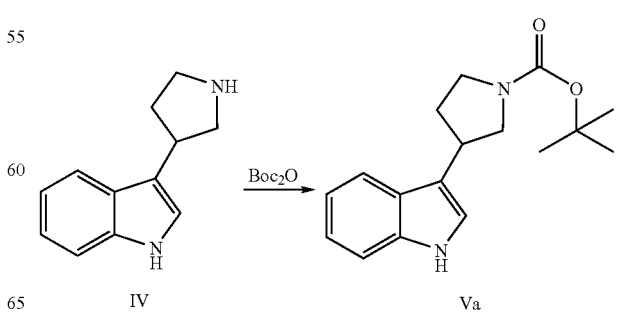

A solution of 19.1 g (87.5 mmol) Boc₂O in 100 ml DCM was added dropwise under a nitrogen atmosphere at 0° C. to a solution of 16.3 g IV in 500 ml DCM within 15 minutes. The reaction mixture was stirred for 2 hours at 0° C. and then overnight at ambient temperature. After purification via column chromatography (first silica gel, Et₂O, second silica gel ethyl acetate/heptane 1:2), 4.1 g (17%) of Va were obtained.

4th Stage:

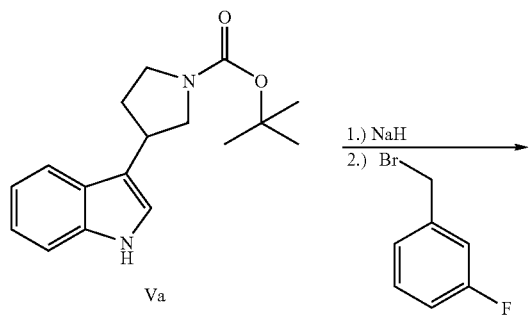

Va 126 mg (3.15 mmol) NaH (60% dispersion in mineral oil) were suspended in 6 ml dry THF under a nitrogen atmosphere. The suspension was cooled to 0° C. and 750 mg Va (2.62 mmol) were added. The mixture was stirred for 3 h at 0° C. and then for a further 30 min at ambient temperature. After repeated cooling to 0° C., 595 mg (3.15 mmol) 3-fluorobenzylbromide were added and the reaction mixture was stirred for 3 hours at 0° C. and then overnight at ambient temperature. Water and saturated aqueous NaCl solution were added and the reaction mixture extracted three times with DCM. The organic phases were dried over Na₂SO₄ and evaporated to dryness. The product (1.08 g) was used without further purification.

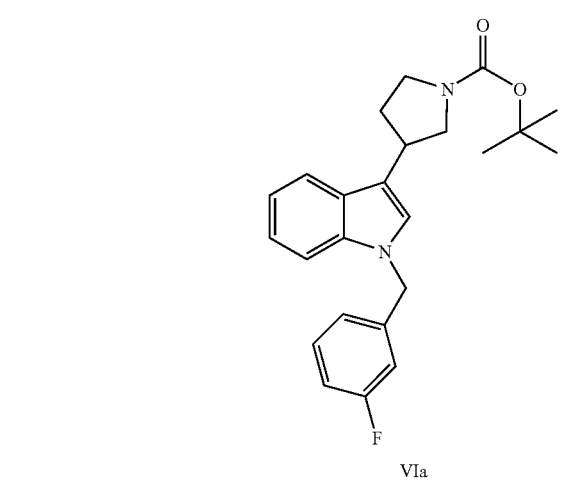

VIa

5th Stage:

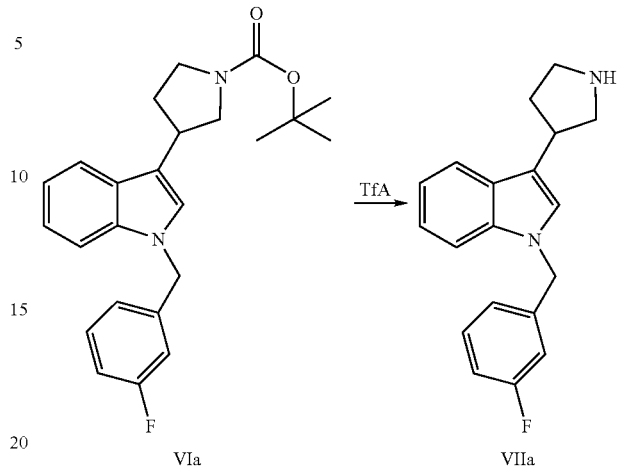

VIa      VIIa

Compound VIa (1.08 g) was dissolved in 5 ml DCM. After adding 5 ml trifluoroacetic acid (Tfa) the mixture was stirred overnight at ambient temperature. After removing the solvent, methanol and heptane were added. After distilling the methanol layer, ethyl acetate and aqueous saturated NaHCO₃ solution were added. The organic layer was separated, dried over Na₂SO₄ and evaporated to dryness. Yield: 870 mg VIIa.

6th Stage:

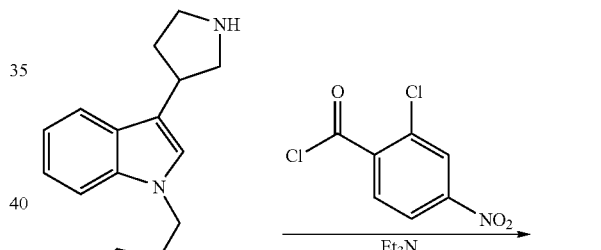

VIIa

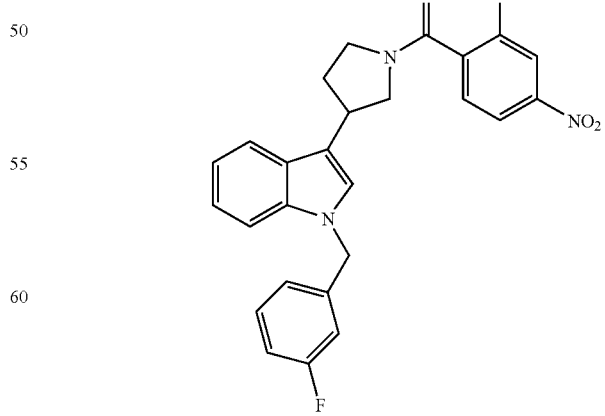

Compound 20

Compound VIIa (0.87 g) was dissolved in 10 ml DCM. 299 mg (2.95 mmol) and 650 mg (2.95 mmol) 2-chloro-4-nitrobenzoylchloride were added and the reaction mixture was stirred overnight under a nitrogen atmosphere at ambient temperature. The solution was extracted in succession with 1 N NaOH, 1 N HCl and saturated aqueous NaHCO$_3$ solution. The organic phase was dried over Na$_2$SO$_4$ and evaporated to dryness. The crude product was purified via column chromatography (first silica gel, MeOH/DCM 1:99, second silica gel, ethyl acetate/hexane 1:2). Yield: 373 mg Compound 20.

The remaining example compounds were similarly produced.

Compounds:

| Compound | R$^1$ | R$^2$ | Name |
|---|---|---|---|
| 1 | 4-trifluoromethyl benzyl | 4-propyl-benzoyl | (4-propyl-phenyl)-{3-[1-(4-trifluoromethyl-benzyl)-1H-indol-3-yl]-pyrrolidin-1-yl}-methanone |
| 2 | 3-methylbutyl | 3,4-dimethoxy-benzoyl | (3,4-dimethoxy-phenyl)-{3-[1-(3-methyl-butyl)-1H-indol-3-yl]-pyrrolidin-1-yl}-methanone |
| 3 | butyl | 2-methyl-6-trifluoromethyl-nicotinoyl | [3-(1-(butyl-1H-indol-3-yl)-pyrrolidin-1-yl]-(2-methyl-6-trifluoromethyl-pyridin-3-yl)-methanone |
| 4 | 3-methoxy-benzyl | 3-phenyl-acryloyl | 1-{3-[1-(3-methoxy-benzyl)-1H-indol-3-yl]-pyrrolidin-1-yl}-3-phenyl-propenone |
| 5 | 4-trifluoromethyl benzyl | 2,3-difluoro-benzoyl | (2,3-difluoro-phenyl)-{3-[1-(4-trifluoromethyl-benzyl)-1H-indol-3-yl]-pyrrolidin-1-yl}-methanone |
| 6 | 3-methylbutyl | 4-trifluoro-methyl-benzoyl | (4-tert-butyl-phenyl)-{3-[1-(3-methyl-butyl)-1H-indol-3-yl]-pyrrolidin-1-yl}-methanone |
| 7 | 4-bromobenzyl | 4-propyl-benzoyl | {3-[1-(4-bromo-benzyl)-1H-indol-3-yl]-pyrrolidin-1-yl}-(4-propyl-phenyl)-methanone |
| 8 | 3-methoxy-benzyl | 2-ethoxy-benzoyl | (2-ethoxy-phenyl)-{3-[1-(3-methoxy-benzyl)-1H-indol-3-yl]-pyrrolidin-1-yl}-methanone |
| 9 | ethyl | 4-trifluoromethyl-3-fluoro-benzoyl | [3-(1-(ethyl-1H-indol-3-yl)-pyrrolidin-1-yl]-(3-fluoro-4-trifluoromethyl-phenyl)-methanone |
| 10 | ethyl | 2,3-dimethyl-benzoyl | (2,3-dimethyl-phenyl)-[3-(1-ethyl-1H-indol-3-yl)-pyrrolidin-1-yl]-methanone |
| 11 | 3-methoxy-benzyl | 2-phenoxy-propionyl | 1-{3-[1-(3-methoxy-benzyl)-1H-indol-3-yl]-pyrrolidin-1-yl}-2-phenoxy-propan-1-one |
| 12 | ethyl | (3-chloro-phenoxy)-acetyl | 2-(3-chloro-phenoxy)-1-[3-(1-ethyl-1H-indol-3-yl)-pyrrolidin-1-yl]-ethanone |
| 13 | 4-cyanobenzyl | 2-phenoxy-propionyl | 4-{3-[1-(2-phenoxy-propionyl)-pyrrolidin-3-yl]-indol-1-ylmethyl}-benzonitrile |
| 14 | 2-N,N-dimethyl-acetamide | 2,4,6-trimethyl-benzyl-sulphonyl | N,N-dimethyl-2-{3-[1-(2,4,6-trimethyl-benzenesulphonyl)-pyrrolidin-3-yl]-indol-1-yl}-acetamide |
| 15 | ethyl | 3,4-dichloro-benzoyl | (3,4-dichloro-phenyl)-[3-(1-ethyl-1H-indol-3-yl)-pyrrolidin-1-yl]-methanone |
| 16 | 2-N,N-dimethyl-acetamide | N-(3-trifluoro-methyl-phenyl)-thio-carbamoyl | N,N-dimethyl-2-{3-[1-(3-trifluoromethyl-phenylthiocarbamoyl)-pyrrolidin-3-yl]-indol-1-yl}-acetamide |
| 17 | 2-N,N-dimethyl-acetamide | 3,4-dichloro-benzylamide | 3-(1-dimethylcarbamoylmethyl-1H-indol-3-yl)-pyrrolidine-1-carboxylic acid 3,4-dichloro-benzylamide |
| 18 | H | 4-(trifluoro-methyl-sulphanyl)-benzoyl | [3-(1H-indol-3-yl)-pyrrolidin-1-yl]-(4-trifluoromethylsulphanyl-phenyl)-methanone |
| 19 | 2-N,N-dimethyl-acetamide | 2,5-dimethoxy-phenylacetyl | 2-(3-{1-[2-(2,5-dimethoxy-phenyl)-acetyl]-pyrrolidin-3-yl}-indol-1-yl)-N,N-dimethyl-acetamide |
| 20 | 3-fluorobenzyl | 2-chloro-4-nitrobenzoyl | (2-chloro-4-nitro-phenyl)-{3-[1-(3-fluoro-benzyl)-1H-indol-3-yl]-pyrrolidin-1-yl}-methanone |
| 21 | 2-N,N-dimethyl-acetamide | pyridin-2-carbonyl | N,N-dimethyl-2-{3-[1-(pyridin-2-carbonyl)-pyrrolidin-3-yl]-indol-1-yl}-acetamide |
| 22 | H | cyclobutyl-carbonyl | cyclobutyl-[3-(1H-indol-3-yl)-pyrrolidin-1-yl]-methanone |
| 23 | 2-N,N-diethyl-acetamide | pentanoyl | N,N-diethyl-2-[3-(1-pentanoyl-pyrrolidin-3-yl)-indol-1-yl]-acetamide |
| 24 | H | 4-nitro-benzyl-sulphonyl | 3-[1-(4-nitro-benzenesulphonyl)-pyrrolidin-3-yl]-1H-indole |
| 25 | 2-N,N-diethyl-acetamide | cyclopentyl-carbonyl | 2-1[3-(1-cyclopentanecarbonyl-pyrrolidin-3-yl)-indol-1-yl]-N,N-diethyl acetamide |
| 26 | methyl | 3-phenyl-acryloyl | 1-[3-(1-methyl-1H-indol-3-yl)-pyrrolidin-1-yl]-3-phenyl-propenone |
| 27 | H | 2-chlorobenzoyl | (2-chloro-phenyl)-[3-(1H-indol-3-yl)-pyrrolidin-1-yl]-methanone |
| 28 | ethyl | 3-pyridyl-carbonyl | [3-(1-(ethyl-1H-indol-3-yl)-pyrrolidin-1-yl]-pyridin-3-yl-methanone |
| 29 | 2-N,N-dimethyl-acetamide | 3-phenyl-2-(tolyl-4-sulphonyl-amino)-propionyl | N,N-dimethyl-2-(3-{1-[3-phenyl-2-(toluene-4-sulphonylamino)-propionyl]-pyrrolidin-3-yl}-indol-1-yl)-acetamide |
| 30 | 2-N,N-dimethyl-acetamide | benzyl-sulphonyl | N,N-dimethyl-2-[3-(1-phenylmethanesulphonyl-pyrrolidin-3-yl)-indol-1-yl]-acetamide |

-continued

| Compound | R¹ | R² | Name |
|---|---|---|---|
| 31 | 4-cyanobenzyl | 2-chloro-6-fluoro-3-methyl-benzyl | 4-{3-[1-(2-chloro-6-fluoro-3-methyl-benzoyl)-pyrrolidin-3-yl]-indol-1-ylmethyl}-benzonitrile |
| 32 | ethyl | 3-(2-chloro-phenyl)-5-methyl-isoxazol-4-carbonyl | [3-(2-chloro-phenyl)-5-methyl-isoxazol-4-yl]-[3-(1-ethyl-1H-indol-3-yl)-pyrrolidin-1-yl]-methanone |
| 33 | 2-cyanobenzyl | 5-tert-butyl-2-methyl-furan-3-carbonyl | 2-{3-[1-(5-tert-butyl-2-methyl-furan-3-carbonyl)pyrrolidin-3-yl]-indol-1-ylmethyl)-benzonitrile |
| 34 | 4-cyanobenzyl | benzo[1,2,5] oxadiazol-5-carbonyl | 4-{3-[1-(benzo[1,2,5]oxadiazole-5-carbonyl)-pyrrolidin-3-yl]-indol-1-ylmethyl}-benzonitrile |
| 35 | ethyl | 3-phenyl-propionyl | 1-[3-(1-ethyl-1H-indol-3-yl)-pyrrolidin-1-yl]-3-phenyl-propan-1-one |
| 36 | 3-methoxy-benzyl | 3-phenyl-propionyl | 1-{3-[1-(3-methoxy-benzyl)-1H-indol-3-yl]-pyrrolidin-1-yl}-3-phenyl-propan-1-one |
| 37 | methyl | 2-methyl-sulphanyl-nicotinoyl | [3-(1-methyl-1H-indol-3-yl)-pyrrolidin-1-yl]-(2-methylsulphanyl-pyridin-3-yl)-methanone |
| 38 | ethyl | 2-chloro-5-trifluoromethyl benzoyl | (2-chloro-5-trifluoromethyl-phenyl)-[3-(1-ethyl-1H-indol-3-yl)-pyrrolidin-1-yl]-methanone |
| 39 | 4-trifluoromethyl benzyl | 2-chloro-4-nitrobenzoyl | (2-chloro-4-nitro-phenyl)-{3-[1-(4-trifluoromethyl-benzyl)-1H-indol-3-yl-pyrrolidin-1-yl}-methanone |
| 40 | methyl | 2-chloro-nicotinoyl | (2-chloro-pyridin-3-yl)-[3-(1-methyl-1H-indol-3-yl)-pyrrolidin-1-yl]-methanone |
| 41 | 3-methoxy-benzyl | methoxy-acetyl | 2-methoxy-1-{3-[1-(3-methoxy-benzyl)-1H-indol-3-yl]-pyrrolidin-1-yl}-ethanone |
| 42 | 3-fluorobenzyl | 4-trifluoro-methyl-2-methyl-nicotinoyl | {3-[1-(3-fluoro-benzyl)-1H-indol-3-yl]-pyrrolidin-1-yl}-(2-methyl-6-trifluoromethyl-pyridin-3-yl)-methanone |
| 43 | 3-methoxy-benzyl | 4-methyl-benzoyl | {3-[1-(3-methoxy-benzyl)-1H-indol-3-yl]-pyrrolidin-1-yl}-p-tolyl-methanone |
| 44 | 3-propinyl | 2-methyl-sulphanyl-nicotinoyl | (2-methylsulphanyl-pyridin-3-yl)-[3-(1-prop-2-inyl-1H-indol-3-yl)-pyrrolidin-1-yl]-methanone |
| 45 | methyl | 4-phenyl-benzoyl | Biphenyl-4-yl-[3-(1-methyl-1H-indol-3-yl)-pyrrolidin-1-yl]-methanone |
| 46 | 3-methoxy-benzyl | (4-chloro-phenyl)-acetyl | 2-(4-chloro-phenyl)-1-{3-[1-(3-methoxy-benzyl)-1H-indol-3-yl]-pyrrolidin-1-yl}-ethanone |
| 47 | methyl | 2,3,4,5,6-pentafluoro-benzoyl | [3-(1-methyl-1H-indol-3-yl)-pyrrolidin-1-yl]-pentafluorophenyl-methanone |
| 48 | ethyl | 4-trifluoro-methyl-benzyl | [3-(11-ethyl-1H-indol-3-yl)-pyrrolidin-1-yl]-(4-trifluoromethyl-phenyl)-methanone |
| 49 | 1-(2-butinyl) | N-(2,5-dimethyl-2H-pyrazol-3-yl)-acetamidyl | 2-[3-(1-but-2-ynyl-1H-indol-3-yl)-pyrrolidin-1-yl]-N-(2,5-dimethyl-2H-pyrazol-3-yl)-acetamide |
| 50 | 3,5-dimethyl-benzyl | N-(3-cyano-4-methyl-thiophen-2-yl)-acetamidyl | N-(3-cyano-4-methyl-thiophen-2-yl)-2-{3-[1-(3,5-dimethyl-benzyl)-1H-indol-3-yl]-pyrrolidin-1-yl}acetamide |
| 51 | 2-N,N-diethyl-acetamide | N-(4-trifluoro-methyl-phenyl)-acetamidyl | N,N-diethyl-2-(3-{1-[(4-trifluoromethyl-phenylcarbamoyl]-methyl]-pyrrolidin-3-yl]-indol-1-yl)-acetamide |
| 52 | ethyl | N-(3-cyano-4-methyl-thiophen-2-yl)-acetamidyl | N-(3-cyano-4-methyl-thiophen-2-yl)-2-[3-(1-ethyl-1H-indol-3-yl)-pyrrolidin-1-yl]-acetamide |
| 53 | 3,4-difluorobenzyl | N-(4-phenyl-5-trifluoro-methyl-thiophen-3-yl)-acetamidyl | 2-{3-[1-(3,4-difluoro-benzyl)-1H-indol-3-yl]-pyrrolidin-1-yl}-N-(4-phenyl-5-trifluiommethyl-thiophen-3-yl)-acetamide |
| 54 | 2-N,N-dimethyl-acetamide | 4-propyl-benzyl-sulphonyl | N,N-dimethyl-2-{3-[1-(4-propyl-benzenesulphonyl)-pyrrolidin-3-yl]-indol-1-yl]-acetamide |
| 55 | 3-methoxy-benzyl | 2-chloro-4-nitrobenzoyl | (2-chloro-4-nitro-phenyl)-{3-[1-(3-methoxy-benzyl)-1H-indol-3-yl]-pyrrolidin-1-yl}-methanone |
| 56 | 3-cyanobenzyl | 4-chloro-benzyl-sulphonyl | 3-(3-[1-(4-chloro-benzenesulphonyl)-pyrrolidin-3-yl]-indol-1-yl methyl}-benzonitrile |
| 57 | 3-methoxy-benzyl | 3,3-dimethyl-butyryl | 1-{3-[1-(3-methoxy-benzyl)-1H-indol-3-yl]-pyrrolidin-1-yl}-3,3-dimethyl-butan-1-one |
| 58 | methyl | (4-chloro-phenyl)-acetyl | 2-(4-chloro-phenyl)-1-[3-(1-methyl-1H-indol-3-yl)-pyrrolidin-1-yl]-ethanone |
| 59 | 3-methoxy-benzyl | 2,6-difluoro-3-methyl-benzoyl | (2,6-difluoro-3-methyl-phenyl)-{3-[1-(3-methoxy-benzyl)-1H-indol-3-yl]-pyrrolidin-1-yl}-methanone |
| 60 | ethyl | 2-methyl-benzoyl | [3-(1-ethyl-1H-indol-3-yl)-pyrrolidin-1-yl]-o-tolyl-methanone |
| 61 | ethyl | 4-fluoro-benzoyl | [3-(1-ethyl-1H-indol-3-yl)-pyrrolidin-1-yl]-(4-fluoro-phenyl)-methanone |
| 62 | n-butyl | 6-chloro-2H-chromen-3-carbonyl | [3-(1-butyl-1H-indol-3-yl)-pyrrolidin-1-yl]-(6-chloro-2H-chromen-3-yl)-methanone |
| 63 | naphthyl-methyl | 2-chloro-6-fluoro-benzoyl | (2-chloro-6-fluoro-phenyl)-[3-(1-naphthalen-2-ylmethyl)-1H-indol-3-yl]-pyrrolidin-1-yl]-methanone |
| 64 | 2-N,N-dimethyl-acetamide | 3-cyclopentyl-propionyl | 2-{3-[1-(3-cyclopentyl-propionyl)-pyrrolidin-3-yl]-indol-1-yl}-N,N-dimethyl-acetamide |
| 65 | 3-methoxy-benzyl | 3-(2-chloro-phenyl)-5-methyl-isoxazol-4-carbonyl | [3-(2-chloro-phenyl)-5-methyl isoxazol-4-yl]-{3-[1-(3-methoxy benzyl)-1H-indol-3-yl]-pyrrolidin-1-yl)methanone |

-continued

| Compound | R¹ | R² | Name |
|---|---|---|---|
| 66 | 3-fluorobenzyl | 1-(4-chloro-phenyl)-5-trifluoromethyl-1H-pyrazol-4-carbonyl | [1-(4,-chloro-phenyl)-5-trifluoromethyl-1H-pyrazol-4-yl]-{3-[1-(3-fluoro-benzyl)-1H-indol-3-yl]-pyrrolidin-1-yl}-methanone |
| 67 | 2-propenyl | 4-methyl-benzoyl | [3-(1-allyl-1H-indol-3-yl)-pyrrolidin-1-yl]-p-tolyl-methanone |
| 68 | 4-fluorobenzyl | pyridin-2-carbonyl | {3-[1-(4-fluoro-benzyl)-1H-indol-3-yl]-pyrrolidin-1-yl}-pyridin-2-yl-methanone |
| 69 | 4-trifluoromethyl benzyl | 3,4-dichloro-benzoyl | (3,4-dichloro-phenyl)-{3-[1-(4-trifluoromethyl-benzyl)-1H-indol-3-yl]-pyrrolidin-1-yl}-methanone |
| 70 | n-butyl | 2,5-dimethoxy-benzoyl | 1-butyl-3-[1-(2,5-dimethoxy-benzenesulphonyl)-pyrrolidin-3-yl]-1H-indole |
| 71 | 2-propenyl | 3,3-dimethyl-butyryl | 1-[3-(1-allyl-1H-indol-3-yl)-pyrrolidin-1-yl]-3,3-dimethyl-butan-1-one |
| 72 | 4-cyano-benzyl | methoxy-acetyl | 4-{3-[1-(2-methoxy-acetyl)-pyrrolidin-3-yl]-indol-1-ylmethyl}-benzonitrile |
| 73 | ethyl | 2,4-difluoro-benzoyl | (2,4-difluoro-phenyl)-[3-(1-ethyl-1H-indol-3-yl)-pyrrolidin-1-yl]-methanone |
| 74 | 4-trifluoromethyl benzyl | 2,3-dimethyl-benzoyl | (2,3-dimethyl-phenyl)-{3-[1-(4-trifluoromethyl-benzyl)-1H-indol-3-yl]-pyrrolidin-1-yl}-methanone |
| 75 | n-butyl | 3-nitro-4-methyl-benzoyl | [3-(1-butyl-1H-indol-3-yl)-pyrrolidin-1-yl]-(4-methyl-3-nitro-phenyl)-methanone |
| 76 | 3-methoxy-benzyl | 4-bromo-3-methyl-benzoyl | (4-bromo-3-methyl-phenyl)-{3-[1-(3-methoxy-benzyl)-1H-indol-3-yl]-pyrrolidin-1-yl}-methanone |
| 77 | n-butyl | (4-chloro-phenoxy)-acetyl | 1-[3-(1-butyl-1H-indol-3-yl)-pyrrolidin-1-yl]-2-(4-chloro-phenoxy)-ethanone |
| 78 | 3-fluorobenzyl | (4-chloro-phenyl)-acetyl | 2-(4-chloro-phenyl)-1-{3-[1-(3-fluoro-benzyl)-1H-indol-3-yl]-pyrrolidin-1-yl}-ethanone |
| 79 | 4-trifluoromethyl benzyl | 4-chloro-benzoyl | (4-chloro-phenyl)-{3-[1-(4-trifluoromethyl-benzyl)-1H-indol-3-yl]-pyrrolidin-1-yl}-methanone |
| 80 | benzyl | 5-methyl-isoxazol-3-carbonyl | [3-(1-benzyl-1H-indol-3-yl)-pyrrolidin-1-yl]-(5-methyl-isoxazol-3-yl)-methanone |
| 81 | benzyl | (4-chloro-phenoxy)-acetyl | 1-[3-(1-benzyl-1H-indol-3-yl)-pyrrolidin-1-yl]-2-(4-chloro-phenoxy)-ethanone |
| 82 | methyl-naphthyl | 4-trifluoro-methyl-benzoyl | [3-(1-naphthalen-2-ylmethyl-1H-indol-3-yl)-pyrrolidin-1-yl]-(4-trifluoromethyl-phenyl)-methanone |
| 83 | 4-trifluoromethyl benzyl | 3-methoxy-benzoyl | (3-methoxy-phenyl)-{3-[1-(4-trifluoromethyl-benzyl)-1H-indol-3-yl]-pyrrolidin-1-yl}-methanone |
| 84 | n-butyl | 3-(2-chloro-phenyl)-acryloyl | 1-[3-(1-butyl-1H-indol-3-yl)-pyrrolidin-1-yl]-3-(2-chloro-phenyl)-propenone |
| 85 | methyl | 2-phenyl-butyryl | 1-[3-(1-methyl-1H-indol-3-yl)-pyrrolidin-1-yl]-2-phenyl-butan-1-one |
| 86 | methyl | 2-chloro-6-fluoro-3-methyl-benzoyl | (2-chloro-6-fluoro-3-methyl-phenyl)-[3-(1-methyl-1H-indol-3-yl)-pyrrolidin-1-yl]-methanone |
| 87 | 2-N,N-dimethyl-acetamide | 3-methoxy-benzoyl | 2-{3-[1-(3-methoxy-benzoyl)-pyrrolidin-3-yl]-indol-1-yl}-N,N-dimethyl-acetamide |
| 88 | 2-N,N-dimethyl-acetamide | 2-fluoro-benzoyl | 2-{3-[1-(2-fluoro-benzoyl)-pyrrolidin-3-yl]-indol-1-yl}-N,N-dimethyl-acetamide |
| 89 | methyl-naphthyl | 3-difluoro-methyl-sulphanyl-benzoyl | (3-difluoromethylsulphanyl-phenyl)-[3-(1-naphthalen-2-ylmethyl-1H-indol-3-yl)-pyrrolidin-1-yl]-methanone |
| 90 | 3-fluorobenzyl | benzo[1,2,5] oxadiazol-5-carbonyl | benzo[1,2,5]oxadiazol-5-yl-{3-[1-(3-fluoro-benzyl)-1H-indol-3-yl]-pyrrolidin-1-yl}-methanone |
| 91 | 4-trifluoromethyl-benzyl | 2-methyl-benzoyl | o-tolyl-{3-[1-(4-trifluoromethyl-benzyl)-1H-indol-3-yl]-pyrrolidin-1-yl}-methanone |
| 92 | 2-N,N-dimethyl-acetamide | 2-trifluoromethyl-benzyl-sulphonyl | N,N-dimethyl-2-{3-[1-(2-trifluoromethyl-benzenesulphonyl)-pyrrolidin-3-yl]-indol-1-yl}-acetamide |
| 93 | n-butyl | 2-phenoxy-propionyl | 1-[3-(1-butyl-1H-indol-3-yl)-pyrrolidin-1-yl]-2-phenoxy-propan-1-one |
| 94 | methyl-naphthyl | 2-chloro-6-fluoro-3-methyl-benzoyl | (6-chloro-2-fluoro-3-methyl-phenyl)-[3-(1-naphthalen-2-ylmethyl-1H-indol-3-yl)-pyrrolidin-1-yl]-methanone |
| 95 | 2-propenyl | 4-trifluoro-methyl-2-methyl-nicotinoyl | [3-(1-allyl-1H-indol-3-yl)-pyrrolidin-1-yl]-(2-methyl-6-trifluoromethyl-pyridin-3-yl)-methanone |
| 96 | n-butyl | 4-propyl-benzoyl | [3-(1-butyl-1H-indol-3-yl)-pyrrolidin-1-yl]-(4-propyl-phenyl)-methanone |
| 97 | 2-N,N-dimethyl-acetamide | 4-chloro-benzoyl | 2-{3-[1-(4-chloro-benzoyl)-pyrrolidin-3-yl]-indol-1-yl}-N,N-dimethyl-acetamide |
| 98 | 3-fluoro-benzyl | 3-phenyl-propionyl | 1-{3-[1-(3-fluoro-benzyl)-1H-indol-3-yl]-pyrrolidin-1-yl}-3-phenyl-propan-1-one |
| 99 | 2-fluoro-benzyl | 1-phenyl-5-propyl-1H-pyrazol-4-carbonyl | {3-[1-(2-fluoro-benzyl)-1H-indol-3-yl]-pyrrolidin-1-yl}-(1-phenyl-5-propyl-1H-pyrazol-4-yl)-methanone |
| 100 | 3-cyanobenzyl | 5-tert-butyl-2-methyl-furan-3-carbonyl | 3-{3-[1-(5-tert-butyl-2-methyl-furan-3-carbonyl)-pyrrolidin-3-yl]-indol-1-ylmethyl}-benzonitrile |
| 101 | 2-fluorobenzyl | 2,4-difluorosulphanyl | 3-[1-(2,4-difluoro-benzenesulphonyl)-pyrrolidin-3-yl]-1-(2-fluoro-benzyl)-1H-indol |
| 102 | 2-N,N-dimethyl-acetamide | 2,6-difluoro-benzyl-sulphanyl | 2-{3-[1-(2,6-difluoro-benzoyl)-pyrrolidin-3-yl]-indol-1-yl}-N,N-dimethyl-acetamide |

-continued

| Compound | R¹ | R² | Name |
|---|---|---|---|
| 103 | n-butyl | butyryl | 1-[3-(1-butyl-1H-indol-3-yl)-pyrrolidin-1-yl]-butan-1-one |
| 104 | 4-cyanobenzyl | 2-propyl-pentanoyl | 4-{3-[1-(2-propyl-pentanoyl)-pyrrolidin-3-yl]-indol-1-ylmethyl)-benzonitrile |
| 105 | 2-propinyl | (4-chloro-phenoxy)-acetyl | 2-(4-chloro-phenoxy)-1-[3-(1-prop-2-ynyl-1H-indol-3-yl)-pyrrolidin-1-yl]-ethanone |
| 106 | methyl | nicotinoyl | [3-(1-methyl-1H-indol-3-yl)-pyrrolidin-1-yl]-pyridin-3-yl-methanone |
| 107 | 3-cyanobenzyl | benzo[1,3]dioxol-5-carbonyl | 3-{3-[1-(benzo[1,3]dioxole-5-carbonyl)-pyrrolidin-3-yl]-indol-1-ylmethyl}-benzonitrile |
| 108 | n-butyl | 2-chloro-5-trifluoro-methyl-benzyl | [3-(1-butyl-1H-indol-3-yl)-pyrrolidin-1-yl]-(2-chloro-5-trifluoromethyl-phenyl)-methanone |
| 109 | 4-trifluoromethyl benzyl | 3-chloro-benzoyl | (3-chloro-phenyl)-{3-[1-(4-trifluoromethyl-benzyl)-1H-indol-3-yl]-pyrrolidin-1-yl}-methanone |
| 110 | 2-N,N-dimethyl-acetamide | 4-bromo-benzoyl | 2-{3-[1-(4-bromo-benzoyl)-pyrrolidin-3-yl]-indol-1-yl}-N,N-dimethyl-acetamide |
| 111 | 2-propinyl | 3-phenyl-acryloyl | 3-phenyl-1-[3-(1-prop-2-ynyl-1H-indol-3-yl)-pyrrolidin-1-yl]-propenone |
| 112 | 3-cyano-benzyl | 3-chloro-2-fluoro-benzoyl | 3-{3-[1-(3-chloro-2-fluoro-benzoyl)-pyrrolidin-3-yl]-indol-1-ylmethyl}-benzonitrile |
| 113 | 3-cyano-benzyl | 2-phenyl-cyclopropan-carbonyl | 3-{3-[1-(2-phenyl-cyclopropanecarbonyl)-pyrrolidin-3-yl]-indol-1-ylmethyl}-benzonitrile |
| 114 | 3-cyano-benzyl | 3-chloro-thiophen-2-carbonyl | 3-{3-[1-(3-chloro-thiophen-2-carbonyl)-pyrrolidin-3-yl]-indol-1-ylmethyl}-benzonitrile |
| 115 | 2-propinyl | 2-trifluoromethyl-benzyl-sulphanyl | 1-prop-2-ynyl-3-[1-(2-trifluoromethyl-benzenesulphonyl)-pyrrolidin-3-yl]-1H-indole |
| 116 | 2-fluorobenzyl | 3-trifluoro-methyl-benzyl-sulphanyl | 1-(2-fluoro-benzyl)-3-[1-(3-trifluoromethyl-benzenesulphonyl)-pyrrolidin-3-yl]-1H-indole |
| 117 | benzyl | 6-chloro-2H-chromen-3-carbonyl | [3-(1-benzyl-1H-indol-3-yl)-pyrrolidin-1-yl]-(6-chloro-2H-chromen-3-yl)-methanone |
| 118 | benzyl | 3,4-difluoro-benzoyl | [3-(1-benzyl-1H-indol-3-yl)-pyrrolidin-1-yl]-(3,4-difluoro-phenyl)-methanone |

Example 2

Biological Testing a) Tests on Serotonin Reuptake Inhibition (5HT Uptake Inhibition)

In order to be able to carry out these in vitro studies, synaptosomes from rats' cerebral cortices were freshly isolated. A "$P_2$" fraction prepared according to Gray and Whittaker's instructions (E. G. Gray and V. P. Whittaker (1962) J. Anat. 76, 79-88) was used in each case. These vesicular particles were isolated from the hypothalamus of male rats' brains for 5HT uptake.

A detailed description of the method may be found in the literature (M. Ch. Frink, H.-H. Hennies, W. Englberger, M. Haurand and B. Wilffert (1996) Arzneim.-Forsch./Drug Res. 46 (III), 11, 1029-1036).

b) Tests on Noradrenalin Reuptake Inhibition (NA Uptake Inhibition)

In order to be able to carry out these in vitro studies, synaptosomes from rats' cerebral cortices were freshly isolated. A "$P_2$" fraction, prepared according to Gray and Whittaker's instructions (E. G. Gray and V. P. Whittaker (1962) J. Anat. 76, 79-88) was used in each case. These vesicular particles were isolated from the hypothalamus of male rats' brains for NA uptake.

A detailed description of the method may be found in the literature (M. Ch. Frink, H.-H. Hennies, W. Englberger, M. Haurand and B. Wilffert (1996) Arzneim.-Frosch./Drug Res. 46 (III), 11, 1029-1036).

c) Binding Tests on the Sodium Channel

Binding Site 2 (BTX Bond)

The binding site 2 of the sodium channel is what is known as the batrachotoxin (BTX) binding site. [$^3$H]-batrachotoxinin A20 α-benzoate (10 nM in a batch) was used as the ligand. These ion channel particles (synaptosomes) were enriched from rat cerebrocortex according to Gray and Whittaker (E. G. Gray and V. P. Whittaker (1962) J. Anat. 76, 79-88). The radioactivity measured in the presence of veratridine (0.3 mM in a batch) is defined as the unspecific bond. Incubation was carried out at 25° C. for 120 min. The assay conditions were adopted according to the publication by Pauwels, Leysen and Laduron (P. J. Pauwels, J. E. Leysen and P. M. Laduron (1986) Eur. J. Pharmacol. 124 291-298).

The $K_D$ value for this binding site is 24.63±1.56 nM. (N=3, i.e. mean±SEM from 3 independent test series which were carried out in triple parallel tests).

a) Inhibition of Serotonin Reuptake

| Compound | 5HT uptake, % inhibition [10 μM] |
|---|---|
| 17 | 43 |
| 18 | 49 |
| 19 | 86 |
| 20 | 89 |
| 21 | 84 |
| 22 | 58 |
| 23 | 49 |
| 24 | 53 |
| 25 | 80 |
| 26 | 62 |
| 27 | 70 |

-continued

| Compound | 5HT uptake, % inhibition [10 μM] |
|---|---|
| 28 | 41 |
| 29 | 63 |
| 30 | 47 |
| 31 | 62 |
| 33 | 87 |
| 34 | 57 |
| 35 | 68 |
| 36 | 42 |
| 37 | 64 |
| 39 | 43 |
| 40 | 66 |
| 41 | 44 |
| 42 | 82 |
| 43 | 48 |
| 44 | 60 |
| 45 | 80 |
| 46 | 46 |
| 47 | 46 |
| 48 | 43 |
| 49 | 68 |
| 50 | 83 |
| 52 | 79 |
| 53 | 55 | b) Inhibition of Noradrenalin Reuptake

| Compound | NA-uptake, inhibition [10 μM] |
|---|---|
| 16 | 50 |
| 18 | 49 |
| 20 | 43 |
| 24 | 59 |
| 26 | 44 |
| 28 | 52 |
| 31 | 41 |
| 32 | 44 |
| 34 | 49 |
| 35 | 48 |
| 37 | 43 |
| 38 | 49 |
| 39 | 41 |
| 40 | 43 |
| 41 | 43 |
| 42 | 58 |
| 44 | 49 |
| 45 | 43 |
| 46 | 20 |
| 48 | 40 |
| 49 | 100 |
| 51 | 57 |
| 52 | 54 | c) Binding to Binding Site 2 of the Sodium Channel

| Compound | BTX bond, % inhibition [10 μM] |
|---|---|
| 1 | 95 |
| 2 | 93 |
| 3 | 93 |
| 4 | 92 |
| 5 | 92 |
| 6 | 91 |
| 7 | 89 |
| 8 | 88 |

-continued

| Compound | BTX bond, % inhibition [10 μM] |
|---|---|
| 9 | 84 |
| 10 | 83 |
| 11 | 83 |
| 12 | 83 |
| 13 | 82 |
| 14 | 80 |
| 15 | 80 |
| 20 | 91 |
| 26 | 93 |
| 31 | 92 |
| 33 | 89 |
| 34 | 91 |
| 35 | 84 |
| 36 | 96 |
| 38 | 89 |
| 39 | 90 |
| 42 | 96 |
| 43 | 92 |
| 45 | 82 |
| 46 | 88 |

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations falling within the scope of the appended claims and equivalents thereof.

What is claimed is:

1. A substituted 3-pyrrolidine-indole compound corresponding to formula I

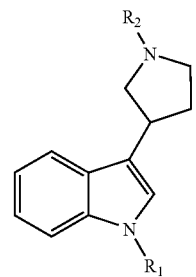

wherein $R^1$ represents H; respectively saturated or unsaturated, branched or unbranched, $C_{1-8}$-alkyl which is unsubstituted or singly or multiply substituted by F, Cl, Br, I, —CN, —N≡C, $NH_2$, NH-alkyl, NH-aryl, NH-heteroaryl, NH-alkyl-aryl, NH-alkyl-heteroaryl, NH-heterocyclyl, NH-alkyl-OH, N(alkyl)$_2$, N(alkyl-aryl)$_2$, N(alkyl-heteroaryl)$_2$, N(heterocyclyl)$_2$, N(alkyl-OH)$_2$, NO, $NO_2$, SH, S-alkyl, S-aryl, S-heteroaryl, S-alkyl-aryl, S-alkyl-heteroaryl, S-heterocyclyl, S-alkyl-OH, S-alkyl-SH, OH, O-alkyl, O-aryl, O-heteroaryl, O-alkyl-aryl, O-alkyl-heteroaryl, O-heterocyclyl, O-alkyl-OH, CHO, C(=O)$C_{1-6}$-alkyl, C(=S)$C_{1-6}$-alkyl, C(=O)aryl, C(=S)aryl, C(=O) $C_{1-6}$-alkyl-aryl, C(=S) $C_{1-6}$-alkyl-aryl, C(=O)-heteroaryl, C(=S)-heteroaryl, C(=O)-heterocyclyl, C(=S)-heterocyclyl. SO-alkyl, $SO_2$-alkyl, $SO_2NH_2$, $SO_3H$, PO(O—$C_{1-6}$-alkyl)$_2$, Si($C_{1-6}$-alkyl)$_3$, Si($C_{3-8}$-cycloalkyl)$_3$, Si($CH_2$-$C_{3-8}$-cycloalkyl)$_3$, Si(phenyl)$_3$, cycloalkyl, aryl, heteroaryl or heterocyclyl; respectively singly or multiply substituted or unsubstituted aryl bound via $C_{1-3}$-alkyl, $C_{3-8}$-cycloalkyl or heteroaryl; or $CH_2CONR^3R^4$;

$R^2$ represents $COR^5$; $SO_2R^6$; $CSNHR^7$; $CONHR^8$; or $CH_2CONHR^9$;

$R^3$ and $R^4$ independently of one another represent respectively saturated or unsaturated, branched or unbranched, unsubstituted or singly or multiply substituted $C_{1-8}$-alkyl; or $R^3$ and $R^4$ together represent $CH_2CH_2OCH_2CH_2$, or $(CH_2)_{3-6}$;

$R^5$ represents branched or unbranched, saturated or unsaturated, substituted or unsubstituted $C_{1-8}$-alkyl; substituted or unsubstituted aryl; substituted or unsubstitute heteroaryl; respectively saturated or unsaturated, substituted or unsubstituted cycloalkyl or heterocyclyl; or

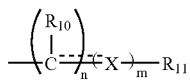

where n=1, 2, 3; m=0, 1; X=O or NH and

----- has the meaning of a single bond or a double bond;

$R^6$ represents respectively substituted or unsubstituted aryl, respectively substituted or unsubstituted heteroaryl, respectively saturated or unsaturated, branched or unbranched, unsubstituted or singly or multiply substituted $C_{1-8}$-alkyl; substituted or unsubstituted, saturated or unsaturated $C_{3-8}$-cycloalkyl; or respectively singly or multiply substituted or unsubstituted aryl bound via $C_{1-3}$-alkyl, $C_{3-8}$-cycloalkyl or heteroaryl;

$R^7$ represents respectively substituted or unsubstituted aryl, respectively substituted or unsubstituted heteroaryl, respectively saturated or unsaturated, branched or unbranched, unsubstituted or singly or multiply substituted $C_{1-8}$-alkyl; substituted or unsubstituted, saturated or unsaturated $C_{3-8}$ cycloalkyl; or respectively singly or multiply substituted or unsubstituted aryl bound via $C_{1-3}$-alkyl, $C_{3-8}$-cycloalkyl or heteroaryl;

$R^8$ represents branched or unbranched, substituted or unsubstituted, saturated or unsaturated $C_{1-8}$-alkyl; substituted or unsubstituted, saturated or unsaturated $C_{3-8}$-cycloalkyl; respectively singly or multiply substituted or unsubstituted trifluoromethyl- or nitrosubstituted phenyl, pyrrolyl, indolyl, furyl, benzofuranyl, thienyl, benzothienyl, pyrazolyl, imidazolyl, thiazolyl, oxazolyl, isoxazoyl, pyridazinyl, pyrimidinyl, pyrazinyl, pyranyl, indazolyl, purinyl, indolizinyl, quinolinyl, isoquinolinyl, quinazolinyl, carbazolyl, phenazinyl, oxadiazolyl, chromenyl or phenothiazinyl; or respectively singly or multiply substituted or unsubstituted aryl bound via $C_{1-3}$-alkyl, $C_{3-8}$-cycloalkyl or heteroaryl;

$R^9$ represents branched or unbranched, substituted or unsubstituted, saturated or unsaturated $C_{1-8}$-alkyl; substituted or unsubstituted, saturated or unsaturated $C_{3-8}$-cycloalkyl; trifluoromethyl- or nitrosubstituted phenyl; respectively singly or multiply substituted or unsubstituted pyrrolyl, indolyl, furyl, benzofuranyl, thienyl, benzothienyl, pyrazolyl, imidazolyl, thiazolyl, oxazolyl, isoxazoyl, pyridazinyl, pyrimidinyl, pyrazinyl, pyranyl, indazolyl, purinyl, indolizinyl, quinolinyl, isoquinolinyl, quinazolinyl, carbazolyl, phenazinyl, chromenyl, oxadiazolyl or phenothiazinyl; or respectively singly or multiply substituted or unsubstituted aryl bound via $C_{1-3}$-alkyl, $C_{3-8}$-cycloalkyl or heteroaryl;

$R^{10}$ represents H; branched or unbranched, substituted or unsubstituted, saturated or unsaturated $C_{1-8}$-alkyl; respectively substituted or unsubstituted aryl or heteroaryl, respectively substituted or unsubstituted benzyl or phenethyl, and $R^{11}$ represents H; branched or unbranched, substituted or unsubstituted, saturated or unsaturated $C_{1-8}$-alkyl; respectively substituted or unsubstituted aryl or heteroaryl, or respectively singly or multiply substituted or unsubstituted aryl bound via $C_{1-3}$-alkyl, $C_{3-8}$-cycloalkyl or heteroaryl;

or a salt thereof with a physiologically acceptable acid.

2. A substituted 3-pyrrolidine-indole compound according to claim 1, wherein said compound is present in the form of a base.

3. A substituted 3-pyrrolidine-indole compound according to claim 1, wherein said compound is present in the form of an individual enantiomer or diastereoisomer.

4. A substituted 3-pyrrolidine-indole compound according to claim 1, wherein said compound is present in the form of a mixture of stereoisomers.

5. A substituted 3-pyrrolidine-indole compound according to claim 1, wherein said compound is present in the form of a racemic mixture.

6. A substituted 3-pyrrolidine-indole compound according to claim 1, wherein the radical $R^2$ represents $COR^5$, $SO_2R^6$ or $CSNHR^7$.

7. A substituted 3-pyrrolidine-indole compound according to claim 1, wherein the radical $R^2$ represents $CONHR^8$ or $CH_2CONHR^9$.

8. A substituted 3-pyrrolidine-indole compound according to claim 1, wherein the radical $R^1$ represents H; respectively saturated or unsaturated, branched or unbranched, unsubstituted or singly or multiply substituted $C_{1-8}$-alkyl; respectively singly or multiply substituted or unsubstituted benzyl or methylnaphthyl; or $CH_2CONR^3R^4$.

9. A substituted 3-pyrrolidine-indole compound according to claim 1, wherein the radical $R^1$ represents benzyl which is unsubstituted or singly or multiply substituted by $CF_3$, Br, F, CN, $OCH_3$ or $CH_3$.

10. A substituted 3-pyrrolidine-indole compound according to claim 1, wherein the radical $R^2$ represents $COR^5$ and $R^5$ represents 4-propylphenyl, 3,4-dimethoxyphenyl, 2-methyl-4-trifluoromethylphenyl-3-pyridine, ethenylphenyl, 2,3-difluorophenyl, 4-tert.-butylphenyl, 2-ethoxyphenyl, 3-fluoro-4-trifluoromethylphenyl, 2,3-dimethylphenyl, phenoxyethyl, phenoxymethyl, 3,4dichlorophenyl, 4-trifluoromethylsulphanylphenyl, 2,5-dimethoxyphenyl, 2-chloro-4-nitrophenyl, 2-chlorophenyl, 4-methyl-N-phenethyl-benzylsulphonamide, 2-chloro-5-fluoro-3-methylphenyl, 3-(2-chlorophenyl)-5-methyl-isoxazole, 5-tert.-butyl-2-methylfuran,-benzo[1,2,5]oxadiazole, phenylpropyl, 2-methylsulphanyl-3-pyridine, 2-chloro-5 trifluoromethylphenyl, methoxymethyl, 4-methylphenyl, biphenyl, 4-chlorobenzyl, 2,3,4,5,6-pentafluorophenyl, 3-chlorophenyl, 4-trifluoromethylphenyl, 2,6-difluoro-3-methylphenyl, 2-methylphenyl, 4-fluorophenyl, 6-chlorochromene, 2-chloro-6-fluorophenyl, ethyl cyclopentyl, 1-(4-chlorophenyl)-5-trifluoromethylpyrazole, 2,4-dichlorophenyl, 2,3-dimethylphenyl, 3-nitro-4-methylphenyl, 4-bromo-3-methylphenyl, (4-chlorophenoxy)methyl, 4-chlorophenyl, 5-methylisoxazole, 3-methoxyphenyl, 2-chlorophenylethenyl, 2-chloro-4-fluoro-3-methylphenyl, 2-fluorophenyl, 3-difluoromethylsulphanylphenyl, 2-fluoro-3-chlorophenyl, cyclopropylphenyl, 1-phenyl-5propylpyrazole, 2,6-difluorophenyl, benzo[1,3]dioxole, 4-bromophenyl, 3-chlorothiophenyl, 2-, 3- or 4-pyridine, phenyl or 3,4-difluorophenyl.

11. A substituted 3-pyrrolidine-indole compound according to claim 1, wherein the radical $R^2$ represents $SO_2R^6$ and $R^6$ represents 2,4,6-dimethylphenyl, 4-nitrophenyl, benzyl, 4-propylphenyl, 4-chlorophenyl, 2-trifluoromethylphenyl, 2,4-difluorophenyl or 3-trifluoromethylphenyl.

12. A substituted 3-pyrrolidine-indole compound according to claim 1, wherein the radical $R^2$ represents $CSNHR^7$ and the radical $R^7$ represents 3-trifluoromethylphenyl.

13. A substituted 3-pyrrolidine-indole compound according to claim 1, wherein the radical $R^2$ represents $CONHR^8$ and the radical $R^8$ represents 3,4-dichlorobenzyl.

14. A substituted 3-pyrrolidine-indole compound according to claim 1, wherein the radical $R^2$ represents $CH_2COR^9$ and $R^9$ represents 2,5-dimethylpyrazole, 3-cyano-4-methylthiophene, 4-trifluoromethylphenyl, or 4-phenyl-5-trifluoromethylthiophene.

15. A substituted 3-pyrrolidine-indole compound selected from the group consisting of:

(4-propyl-phenyl)-{3-[1-(4-trifluoromethyl-benzyl)-1H-indol-3-yl]-pyrrolidin-1-yl}-methanone
(3,4-dimethoxy-phenyl)-{3-[1-(3-methyl-butyl)-1H-indol-3-yl]-pyrrolidin-1-yl}-methanone
[3-(1-butyl-1H-indol-3-yl)-pyrrolidin-1-yl]-(2-methyl-6-trifluoromethyl-pyridin-3-yl)-methanone
1-{3-[1-(3-methoxy-benzyl)-1H-indol-3-yl]-pyrrolidin-1-yl}-3-phenyl-propenone
(2,3-difluoro-phenyl)-{3-[1-(4-trifluoromethyl-benzyl)-1H-indol-3-yl]-pyrrolidin-1-yl}-methanone
(4-tert-butyl-phenyl)-{3-[1-(3-methyl-butyl)-1H-indol-3-yl]-pyrrolidin-1-yl}-methanone
{3-[1-(4-bromo-benzyl)-1H-indol-3-yl]-pyrrolidin-1-yl}-(4-propyl-phenyl)-methanone
(2-ethoxy-phenyl)-{3-[1-(3-methoxy-benzyl)-1H-indol-3-yl]-pyrrolidin-1-yl}-methanone
[3-(1-ethyl-1H-indol-3-yl)-pyrrolidin-1-yl]-(3-fluoro-4-trifluoromethyl-phenyl)-methanone
(2,3-dimethyl-phenyl)-[3-(1-ethyl-1H-indol-3-yl)-pyrrolidin-1-yl]-methanone
1-{3-[1-(3-methoxy-benzyl)-1H-indol-3-yl]-pyrrolidin-1-yl}-2-phenoxy-propan-1-one
2-(3-chloro-phenoxy)-1-[3-(1-ethyl-1H-indol-3-yl)-pyrrolidin-1-yl]-ethanone
4-{3-[1-(2-phenoxy-propionyl)-pyrrolidin-3-yl]-indol-1-ylmethyl}-benzonitrile
N,N-dimethyl-2-{3-[1-(2,4,6-trimethyl-benzenesulphonyl)-pyrrolidin-3-yl]-indol-1-yl}-acetamide
(3,4-dichloro-phenyl)-[3-(1-ethyl-1H-indol-3-yl)-pyrrolidin-1-yl]-methanone
N,N-dimethyl-2-{3-[1-(3-trifluoromethyl-phenylthiocarbamoyl)-pyrrolidin-3-yl]-indol-1-yl}-acetamide
3-(1-dimethylcarbanmoylmethyl-1H-indol-3-yl)-pyrrolidin-1-carboxylic acid 3,4-dichloro-benzylamide
[3-(1H-indol-3-yl)-pyrrolidin-1-yl]-(4-trifluoromethyl-sulphanyl-phenyl)-methanone
2-(3-{1-[2-(2,5-dimethoxy-phenyl)-acetyl]-pyrrolidin-3-yl}-indol-1-yl)-N,N-dimethyl-acetamide
(2-chloro-4-nitro-phenyl)-{3-[1-(3-fluoro-benzyl)-1H-indol-3-yl]-pyrrolidin-1-yl}-methanone
N,N-dimethyl-2-{3-[1-(pyridin-2-carbonyl)-pyrrolidin-3-yl]-indol-1-yl}-acetamide
cyclobutyl-[3-(1H-indol-3-yl)-pyrrolidin-1-yl]-methanone
N,N-diethyl-2-[3-(1-pentanoyl-pyrrolidin-3-yl)-indol-1-yl]-acetamide
3-[1-(4-nitrobenzenesulphonyl)-pyrrolidin-3-yl]-1H-indole
2-[3-(1-cyclopentanecarbonyl-pyrrolidin-3-yl)-indol-1-yl]-N,N-diethyl-acetamide
1-[3-(1-methyl-1H-indol-3-yl)-pyrrolidin-1-yl]-3-phenyl-propenone
(2-chloro-phenyl)-[3-(1H-indol-3-yl)-pyrrolidin-1-yl]-methanone
[3-(1-ethyl-1H-indol-3-yl)-pyrrolidin-1-yl]-pyridin-3-yl-methanone
N,N-dimethyl-2-(3-{1-[3-phenyl-2-(toluene-4-sulphonylamino)-propionyl]-pyrrolidin-3-yl}-indol-1-yl)-acetamide
N,N-dimethyl-2-[3-(1-phenylmethanesulphonyl-pyrrolidin-3-yl)-indol-1-yl]-acetamide
4-{3-[1-(2-chloro-6-fluoro-3-methyl-benzoyl)-pyrrolidin-3-yl]-indol-1-ylmethyl}-benzonitrile
[3-(2-chloro-phenyl)-5-methyl-isoxazol-4-yl]-[3-(1-ethyl-1H-indol-3-yl)-pyrrolidin-1yl]-methanone
2-{3-[1-(5-tert-butyl-2-methyl-furan-3-carbonyl)-pyrrolidin-3-yl]-indol-1-ylmethyl}-benzonitrile
4-{3-[1-(benzo[1,2,5]oxadiazole-5-carbonyl)-pyrrolidin-3-yl]-indol-1-ylmethyl}-benzonitrile
1-[3-(1-ethyl-1H-indol-3-yl)-pyrrolidin-1-yl]-3-phenyl-propan-1-one
1-{3-[1-(3-methoxy-benzyl)-1H-indol-3-yl]-pyrrolidin-1-yl}-3-phenyl-propan-1-one
[3-(1-methyl-1H-indol-3-yl)-pyrrolidin-1-yl]-(2-methyl-sulphanyl-pyridin-3-yl)-methanone
(2-chloro-5-trifluoromethyl-phenyl)-[3-(1-ethyl-i H-indol-3-yl)-pyrrolidin-1-yl]-methanone
(2-chloro-4-nitro-phenyl)-{3-[1-(4-trifluoromethyl-benzyl)-1H-indol-3-yl]-pyrrolidin-1 yl}-methanone
(2-chloro-pyridin-3-yl)-[3-(1-methyl-1H-indol-3-yl)-pyrrolidin-1-yl]-methanone
2-methoxy-1-{3-[1-(3-methoxy-benzyl)-1H-indol-3-yl]-pyrrolidin-1-yl}-ethanone
{3-[1-(3-fluoro-benzyl)-1H-indol-3-yl]-pyrrolidin-1-yl}-(2-methyl-6-trifluoromethylpyridin-3-yl)-methanone
{3-[1-(3-methoxy-benzyl)-1H-indol-3-yl]-pyrrolidin-1-yl}-p-tolyl-methanone
(2-methylsulphanyl-pyridin-3-yl)-[3-(1-prop-2-ynyl-1H-indol-3-yl)-pyrrolidin-1-yl]-methanone
biphenyl-4-yl-[3-(1-methyl-1H-indol-3-yl)-pyrrolidin-1-yl]-methanone
2-(4-chloro-phenyl)-1-{3-[1-(3-methoxy-benzyl)-1H-indol-3-yl]-pyrrolidin-1-yl}-ethanone
[3-(1-methyl-1H-indol-3-yl)-pyrrolidin-1-yl]-pentafluorophenyl-methanone
[3-(1-ethyl-1H-indol-3-yl)-pyrrolidin-1-yl]-(4-trifluoromethyl-phenyl)-methanone
2-[3-(1-but-2-ynyl-1H-indol-3-yl)-pyrrolidin-1-yl]-N-(2,5-dimethyl-2H-pyrazol-3-yl)-acetamide
N-(3-cyano-4-methyl-thiophen-2-yl)-2-{3-[1-(3,5-dimethyl-benzyl)-1H-indol-3-yl]pyrrolidin-1-yl}-acetamide
N,N-diethyl-2-(3-{1-[(4-trifluoromethyl-phenyl carbamoyl)-methyl]-pyrrolidin-3-yl}-indol-1-yl)-acetamide N-(3-cyano-4-methyl-thiophen-2-yl)-2-[3-(1-ethyl-1H-indol-3-yl)-pyrrolidin-1-yl]-acetamide
2-{3-[1-(3,4-difluoro-benzyl)-1H-indol-3-yl]-pyrrolidin-1-yl}-N-(4-phenyl-5-trifluoromethyl-thiophen-3-yl)-acetamide
N,N-dimethyl-2-{3-[1-(4-propyl-benzenesulphonyl)-pyrrolidin-3-yl]-indol-1-yl}-acetamide
(2-chloro-4-nitro-phenyl)-{3-[1-(3-methoxy-benzyl)-1H-indol-3-yl]-pyrrolidin-1-yl}-methanone
3-{3-[1-(4-chloro-benzenesulphonyl)-pyrrolidin-3-yl]-indol-1-ylmethyl}-benzonitrile
1-{3-[1-(3-methoxy-benzyl)-1H-indol-3-yl]-pyrrolidin-1-yl}-3,3-dimethyl-butan-1-one
2-(4-chloro-phenyl)-1-[3-(1-methyl-1H-indol-3-yl)-pyrrolidin-1-yl]-ethanone
(2,6-difluoro-3-methyl-phenyl)-{3-[1-(3-methoxy-benzyl)-1H-indol-3-yl]-pyrrolidin-1-yl}-methanone
[3-(1-ethyl-1H-indol-3-yl)-pyrrolidin-1-yl]-o-tolyl-methanone
[3-(1-ethyl-1H-indol-3-yl)-pyrrolidin-1-yl]-(4-fluoro-phenyl)-methanone
[3-(1-butyl-1H-indol-3-yl)-pyrrolidin-1-yl]-(6-chloro-2H-chromen-3-yl)-methanone
(2-chloro-6-fluoro-phenyl)-[3-(1-naphthalen-2-ylmethyl-1H-indol-3-yl)-pyrrolidin-1-yl]-methanone
2-{3-[1-(3-cyclopentyl-propionyl)-pyrrolidin-3-yl]-indol-1-yl}-N,N-dimethyl-acetamide
[3-(2-chloro-phenyl)-5-methyl-isoxazol-4-yl]-{3-[1-(3-methoxy-benzyl)-1H-indol-3-yl]-pyrrolidin-1-yl}-methanone
[1-(4-chloro-phenyl)-5-trifluoromethyl-1H-pyrazol-4-yl]-{3-[1-(3-fluoro-benzyl)-1H-indol-3-yl]-pyrrolidin-1-yl}-methanone
[3-(1-allyl-1H-indol-3-yl)-pyrrolidin-1-yl]-p-tolyl-methanone
{3-[1-(4-fluoro-benzyl)-1H-indol-3-yl]-pyrrolidin-1-yl}-pyridin-2-yl-methanone
(3,4-dichloro-phenyl)-{3-[1-(4-trifluoromethyl-benzyl)-1H-indol-3-yl]-pyrrolidin-1-yl}-methanone
1-butyl-3-[1-(2,5-dimethoxy-benzenesulphonyl)-pyrrolidin-3-yl]-1H-indole
1-[3-(1-allyl-1H-indol-3-yl)-pyrrolidin-1-yl]-3,3-dimethyl-butan-1-one
4-{3-[1-(2-methoxy-acetyl)-pyrrolidin-3-yl]-indol-1-ylmethyl}-benzonitrile
(2,4-difluoro-phenyl)-[3-(1-ethyl-1H-indol-3-yl)-pyrrolidin-1-yl]-methanone
(2,3-dimethyl-phenyl)-{3-[1-(4-trifluoromethyl-benzyl)-1H-indol-3-yl]-pyrrolidin-1-yl}-methanone
[3-(1-butyl-1H-indol-3-yl)-pyrrolidin-1-yl]-(4-methyl-3-nitro-phenyl)-methanone
(4-bromo-3-methyl-phenyl)-{3-[1-(3-methoxy-benzyl)-1H-indol-3-yl]-pyrrolidin-1-yl}-methanone
1-[3-(1-butyl-1H-indol-3-yl)-pyrrolidin-1-yl]-2-(4-chloro-phenoxy)-ethanone
2-(4-chloro-phenyl)-1-{3-[1-(3-fluoro-benzyl)-1H-indol-3-yl]-pyrrolidin-1-yl}-ethanone
(4-chloro-phenyl)-{3-[1-(4-trifluoromethyl-benzyl)-1H-indol-3-yl]-pyrrolidin-1-yl}-methanone
[3-(1-benzyl-1H-indol-3-yl)-pyrrolidin-1-yl]-(5-methyl-isoxazol-3-yl )-methanone
1-[3-(1-benzyl-1H-indol-3-yl)-pyrrolidin-1-yl]-2-(4-chloro-phenoxy)-ethanone
[3-(1-naphthalen-2-ylmethyl-1H-indol-3-yl)-pyrrolidin-1-yl]-(4-trifluoromethylphenyl)-methanone
(3-methoxy-phenyl)-(3-[1-(4-trifluoromethyl-benzyl)-1H-indol-3-yl]-pyrrolidin-1-yl}-methanone
1-[3-(1-butyl-1H-indol-3-yl)-pyrrolidin-1-yl]-3-(2-chloro-phenyl)-propenone
1-[3-(1-methyl-1H-indol-3-yl)-pyrrolidin-1-yl]-2-phenyl-butane-1-one
(2-chloro-6-fluoro-3-methyl-phenyl)-[3-(1-methyl-1H-indol-3-yl)-pyrrolidin-1-yl]-methanone
2-{3-[1-(3-methoxy-benzoyl)-pyrrolidin-3-yl]-indol-1-yl}-N,N-dimethyl-acetamide
2-{3-[1-(2-fluoro-benzoyl)-pyrrolidin-3-yl]-indol-1-yl}-N,N-dimethyl-acetamide
(3-difluoromethylsulphanyl-phenyl)-[3-(1-naphthalen-2-ylmethyl-1H-indol-3-yl)-pyrrolidin-1-yl]-methanone
benzo[1,2,5]oxadiazol-5-yl-{3-[1-(3-fluoro-benzyl)-1H-indol-3-yl]-pyrrolidin-1-yl}-methanone
o-tolyl-{3-[1-(4-trifluoromethyl-benzyl)-1H-indol-3-yl]-pyrrolidin-1-yl}-methanone
N,N-dimethyl-2-{3-[1-(2-trifluoromethyl-benzenesulphonyl)-pyrrolidin-3-yl]-indol-1-yl}-acetamide
1-[3-(1-butyl-1H-indol-3-yl)-pyrrolidin-1-yl]-2-phenoxy-propan-1-one
(6-chloro-2-fluoro-3-methyl-phenyl)-[3-(1-naphthalen-2-ylmethyl-1H-indol-3-yl)-pyrrolidin-1-yl]-methanone
[3-(1-allyl-1H-indol-3-yl)-pyrrolidin-1-yl]-(2-methyl-6-trifluoromethyl-pyridin-3-yl)-methanone
[3-(1-butyl-1H-indol-3-yl)-pyrrolidin-1-yl]-(4-propyl-phenyl)-methanone
2-{3-[1-(4-chloro-benzoyl)-pyrrolidin-3-yl]-indol-1-yl)-N,N-dimethyl-acetamide
1-{3-[1-(3-fluoro-benzyl)-1H-indol-3-yl]-pyrrolidin-1-yl}-3-phenyl-propan-1-one
{3-[1-(2-fluoro-benzyl)-1H-indol-3-yl]-pyrrolidin-1-yl}-(1-phenyl-5-propyl-1H-pyrazol-4-yl)-methanone
3-{3-[1-(5-tert-butyl-2-methyl-furan-3-carbonyl)-pyrrolidin-3-yl]-indol-1-ylmethyl}-benzonitrile
3-[1-(2,4-difluoro-benzenesulphonyl)-pyrrolidin-3-yl]-1-(2-fluoro-benzyl)-1H-indole
2-{3-[1-(2,6-difluoro-benzoyl)-pyrrolidin-3-yl]-indol-1-yl}-N,N-dimethyl-acetamide
1-[3-(1-butyl-1H-indol-3-yl)-pyrrolidin-1-yl]-butane-1-one
4-{3-[1-(2-propyl-pentanoyl)-pyrrolidin-3-yl]-indol-1-ylmethyl}-benzonitrile
2-(4-chloro-phenoxy)-1-[3-(1-prop-2-ynyl-1H-indol-3-yl)-pyrrolidin-1-yl]-ethanone
[3-(1-methyl-1H-indol-3-yl)-pyrrolidin-1-yl]-pyridin-3-yl-methanone
3-{3-[1-(benzo[1,3]dioxole-5-carbonyl)-pyrrolidin-3-yl]-indol-1-ylmethyl}-benzonitrile
[3-(1-butyl-1H-indol-3-yl)-pyrrolidin-1-yl]-(2-chloro-5-trifluoromethyl-phenyl)-methanone
(3-chloro-phenyl)-{3-[1-(4-trifluoromethyl-benzyl)-1H-indol-3-yl]-pyrrolidin-1-yl}-methanone
2-{3-[1-(4-bromo-benzoyl)-pyrrolidin-3-yl]-indol-1-yl}-N,N-dimethyl-acetamide
3-phenyl-1-[3-(1-prop-2-ynyl-1H-indol-3-yl)-pyrrolidin-1-yl]-propenone
3-{3-[1-(3-chloro-2-fluoro-benzoyl)-pyrrolidin-3-yl]-indol-1-ylmethyl}-benzonitrile
3-{3-[1-(2-phenyl-cyclopropanecarbonyl)-pyrrolidin-3-yl]-indol-1-ylmethyl}-benzonitrile
3-{3-[1-(3-chloro-thiophene-2-carbonyl)-pyrrolidin-3-yl]-indol-1-ylmethyl}-benzonitrile
1-prop-2-ynyl-3-[1-(2-trifluoromethyl-benzenesulphonyl)-pyrrolidin-3-yl]-1H-indole
1-(2-fluoro-benzyl)-3-[1-(3-trifluoromethyl-benzenesulphonyl)-pyrrolidin-3-yl]-1H-indole

[3-(1-benzyl-1H-indol-3-yl)-pyrrolidin-1-yl]-(6-chloro-2H-chromen-3-yl)-methanone and

[3-(1-benzyl-1H-indol-3-yl)-pyrrolidin-1-yl]-(3,4-difluoro-phenyl)-methanone and salts therof with a physiologically acceptable acid.

16. A composition comprising a 3-pyrrolidine-indole compound according to claim 1 and one or more suitable additives or auxiliaries.

* * * * *